United States Patent
Wang et al.

(10) Patent No.: US 9,562,269 B2
(45) Date of Patent: Feb. 7, 2017

(54) HAPLOTYING OF HLA LOCI WITH ULTRA-DEEP SHOTGUN SEQUENCING

(71) Applicant: The Board of Trustees of the Leland Stanford Junior University, Palo Alto, CA (US)

(72) Inventors: Chunlin Wang, Palo Alto, CA (US); Michael N. Mindrinos, Palo Alto, CA (US); Mark M. Davis, Atherton, CA (US); Ronald W. Davis, Palo Alto, CA (US); Sujatha Krishnakumar, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/161,515

(22) Filed: Jan. 22, 2014

(65) Prior Publication Data
US 2014/0206547 A1   Jul. 24, 2014

Related U.S. Application Data

(60) Provisional application No. 61/755,231, filed on Jan. 22, 2013.

(51) Int. Cl.
*C12Q 1/68* (2006.01)
*G06F 19/22* (2011.01)
*G06F 19/18* (2011.01)

(52) U.S. Cl.
CPC ............ *C12Q 1/6881* (2013.01); *G06F 19/18* (2013.01); *G06F 19/22* (2013.01); *C12Q 2600/118* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

| | | | |
|---|---|---|---|
| 5,750,341 A | 5/1998 | Macevicz |
| 5,969,119 A | 10/1999 | Macevicz |
| 6,306,597 B1 | 10/2001 | Macevicz |
| 7,170,050 B2 | 1/2007 | Turner et al. |
| 7,211,390 B2 | 5/2007 | Rothberg et al. |
| 7,244,559 B2 | 7/2007 | Rothberg et al. |
| 7,244,567 B2 | 7/2007 | Chen et al. |
| 7,264,929 B2 | 9/2007 | Rothberg et al. |
| 7,276,720 B2 | 10/2007 | Ulmer |
| 7,302,146 B2 | 11/2007 | Turner et al. |
| 7,313,308 B2 | 12/2007 | Turner et al. |
| 7,315,019 B2 | 1/2008 | Turner et al. |
| 7,323,305 B2 | 1/2008 | Leamon et al. |
| 7,335,762 B2 | 2/2008 | Rothberg et al. |
| 7,405,281 B2 | 7/2008 | Xu et al. |
| 7,462,452 B2 | 12/2008 | Williams et al. |
| 7,462,468 B1 | 12/2008 | Williams et al. |
| 7,476,503 B2 | 1/2009 | Turner et al. |
| 7,476,504 B2 | 1/2009 | Turner |
| 7,491,498 B2 | 2/2009 | Lapidus et al. |
| 7,501,245 B2 | 3/2009 | Quake et al. |
| 2006/0024678 A1 | 2/2006 | Buzby |
| 2006/0024711 A1 | 2/2006 | Lapidus et al. |
| 2006/0286566 A1 | 12/2006 | Lapidus et al. |
| 2008/0087826 A1 | 4/2008 | Harris et al. |
| 2008/0103058 A1 | 5/2008 | Siddiqi |
| 2008/0206764 A1 | 8/2008 | Williams et al. |
| 2008/0213770 A1 | 9/2008 | Williams et al. |
| 2009/0024331 A1 | 1/2009 | Tomaney et al. |
| 2009/0029385 A1 | 1/2009 | Christians et al. |
| 2009/0061439 A1 | 3/2009 | Buzby |
| 2009/0068655 A1 | 3/2009 | Williams |
| 2009/0176235 A1 | 7/2009 | Cargill et al. |
| 2012/0264627 A1 | 10/2012 | Reinherz et al. |
| 2015/0225789 A1 | 8/2015 | Wang et al. |

FOREIGN PATENT DOCUMENTS

| | | |
|---|---|---|
| EP | 2314715 A2 | 4/2011 |
| WO | 2009/032948 A2 | 3/2009 |
| WO | WO 2014/116729 A2 | 7/2014 |

OTHER PUBLICATIONS

Lind et al., Next-generation sequencing: the solution for high-resolution, unambiguous human leukocyte antigen typing, Hum Immunol. Oct. 2010;71(10):1033-42. doi: 10.1016/j.humimm.2010.06.016. Epub Aug. 5, 2010.*
Campbell, "Nested Primers for PCR", Department of Biology, Davidson College (2002), retrieved Jul. 17, 2014, http://www.biodavidson.edu/courses/genomics/method/nestedpcr.html.
Jinushi; et al., "Homo sapiens MHC class I polypeptide-related sequence A (MICA), RefSeqGene on chromosome 6", NCBI Reference Sequence: NG_034139.1 (Jun. 2014), retrieved Jul. 18, 2014: http://www.ncbi.nlm.nih.gov/nucleotide/297515495?report=genebank&log$=nuclalign&blast_rank=1&RID=WJJTRVRM015.
"Homo sapiens MHC class I polypeptide-related sequence B (MICB), RefSeqGene on chromosome 6", NCBI Reference Sequence: NG_021405.1 (May 2014), retrieved Jul. 18, 2014: http://www.ncbi.nlm.nih.gov/nucleotide/645912997?report=genbank&log$=nuclalign&blast_rank=1&RID=WJHZ21KF01R.
Mindrinos, et al. High Throughput, High Fidelity HLA Typing With Deep Sequencing. Poster 2012.
Ronaghi, et al. A sequencing method based on real-time pyrophosphate. Science. Jul. 17, 1998;281(5375):363, 365.

(Continued)

*Primary Examiner* — Aaron Priest
(74) *Attorney, Agent, or Firm* — Pamela J. Sherwood; Bozicevic, Field & Francis LLP

(57) ABSTRACT

Methods are provided to determine the entire genomic region of a particular HLA locus including both intron and exons. The resultant consensus sequences provides linkage information between different exons, and produces the unique sequence from each of the two genes from the individual sample being typed. The sequence information in intron regions along with the exon sequences provides an accurate HLA haplotype.

9 Claims, 11 Drawing Sheets

(56) References Cited

OTHER PUBLICATIONS

Ronaghi, et al. Real-time DNA sequencing using detection of pyrophosphate release. Anal Biochem. Nov. 1, 1996;242(1):84-9.
Bentley et al., "High-Resolution, High-Throughput HLA Genotyping by Next Generation Sequencing", Tissue Antigens (2009), 74(5):393-403.
Erlich et al., "Next-Generation Sequencing for HLA Typing of Class I Loci", BMC Genomics (2011), 12:42.
Gabriel et al., "Rapid High-Throughput Human Leukocyte Antigen Typing by Massively Parallel Pyrosequencing for High-Resolution Allele Identification", Hum Immunol (2009), 70:960-964.
Holcomb et al., "A Multi-Site Study Using High-Resolution HLA Genotyping by Next Generation Sequencing", Tissue Antigens (2011), 77(3):206-217.
Lind et al., "Next Generation Sequencing: The Solution for High-Resolution, Unambiguous Human Leukocyte Antigen Typing", Hum Immunol (2010), 71(10):1033-1042.
Margulies et al., "Genome Sequencing in Microfabricated High-Density Picolitre Reactors", Nature (2005), 437:376-380.
Wang et al., "High-Throughput, High-Fidelity HLA Genotyping with Deep Sequencing", PNAS (2012), 109(22):8676-8681.
U.S. Appl. No. 14/749,491, filed Jun. 24, 2015, Wang et al.
Ausubel, et al. Current Protocols in Molecular Biology, 1994.
International search report dated Aug. 12, 2014 for PCT Application No. US2014/012585.
Sambrook, et al. Molecular Cloning, A Laboratory Manual. vol. 2. New York: Cold Spring Harbor Laboratory Press, 1989.
He et al., "Optimal algorithms for haplotype assembly from whole-genome sequence data.", Bioinformatics 2010, pp. i183-i190, vol. 26, Oxford University Press, Oxford, United Kingdom.

\* cited by examiner

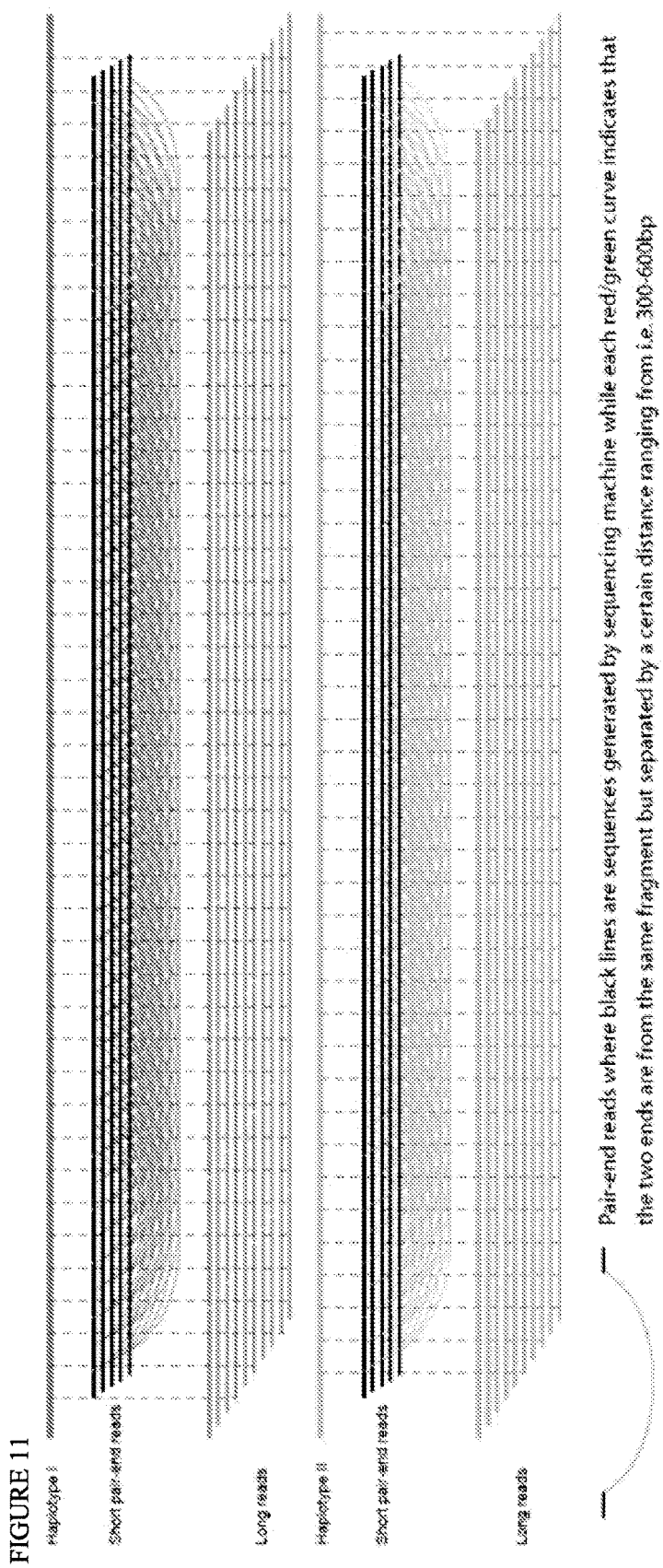

HAPLOTYING OF HLA LOCI WITH ULTRA-DEEP SHOTGUN SEQUENCING

GOVERNMENT RIGHTS

This invention was made with Government support under contract no. HDTRA1-11-1-0058 awarded by the Defense Threat Reduction Agency and under contracts nos. AI090019, AR059760, GM062119, and HG000205 awarded by the National Institutes of Health. The Government has certain rights in the invention.

BACKGROUND OF THE INVENTION

The human leukocyte antigen complex, also known as the major histocompatibility complex, spans approximately 3.5 million base pairs on the short arm of chromosome 6. It is divisible into 3 separate regions, which contain the class I, the class II and the class III genes, respectively. There are 20 genes in the class I region, including the classical MHC molecules designated HLA-A, HLA-B and HLA-C. In addition are the nonclassical class I genes: HLA-E, HLA-F, HLA-G, HLA-H, HLA-J, HLA-X, and MIC. The class II region contains the HLA-DP, HLA-DQ and HLA-DR loci, which encode the α and β chains of the classical class II MHC molecules designated HLA-DR, DP and DQ. Nonclassical genes designated DM, DN and DO have also been identified within class II. The class III region contains a heterogeneous collection of more than 36 genes. The loci constituting the MHC are highly polymorphic. Several hundred different allelic variants of class I and class II MHC molecules have been identified in humans.

The specific protein sequences of the highly polymorphic HLA locus play a major role in determining histocompatibility of transplants, as well as important insight into susceptibility of a number of immune related disorders, including celiac disease, rheumatoid arthritis, insulin dependent diabetes mellitus, multiple sclerosis and the like. Matching of donor and recipient HLA-DR and DQ alleles prior to allogeneic transplantation has a particularly important influence on allograft survival. Therefore, HLA matching is universally required as a clinical prerequisite for renal and bone marrow transplantation as well as cord blood applications.

Conventional matching has been performed by serological and cellular typing. For example, in a microcytotoxicity test, white blood cells from the potential donor and recipient are distributed in a microtiter plate and monoclonal antibodies specific for class I and class II MHC alleles are added to different wells. Thereafter, complement is added to the wells and cytotoxicity is assessed by uptake or exclusion to various dyes by the cells. However, serological typing is frequently problematic, due to the availability and crossreactivity of alloantisera and because live cells are required. A high degree of error and variability is also inherent in serological typing. Therefore, DNA typing is becoming more widely used as an adjunct, or alternative, to serological tests.

In some methods, PCR amplified products are hybridized with sequence-specific oligonucleotide probes (PCR-SSO) to distinguish between HLA alleles. This method requires a PCR product of the HLA locus of interest be produced and then dotted onto nitrocellulose membranes or strips. Then each membrane is hybridized with a sequence specific probe, washed, and then analyzed by exposure to x-ray film or by colorimetric assay depending on the method of detection. Hybridization and detection methods for PCR-SSO typing include the use of non-radioactive labeled probes, microplate formats, etc., and automated large scale HLA class II typing.

More recently, a molecular typing method using sequence specific primer amplification (PCR-SSP) has been described. In PCR-SSP, allelic sequence specific primers amplify only the complementary template allele, allowing genetic variability to be detected with a high degree of resolution. This method allows determination of HLA type simply by whether or not amplification products are present or absent following PCR. In PCR-SSP, detection of the amplification products may be done by agarose gel electrophoresis.

Currently, direct DNA sequencing or "sequence based typing" (SBT) provides the highest resolution to discriminate these alleles at the nucleotide level, where minor differences in sequence have great impact on the phenotype of the HLA genes. However, HLA genes span between 5 Kb to 15 Kb interspersed between introns and exons in human genome. All current DNA sequencing approaches target one or a few of disjoined exons in the genomic DNA and not the processed RNA from these genes because of the inherent difficulty of handling RNA in patient samples. Since each individual is diploid, it is important to characterize the unique sequence from each gene to understand how these changes are reflected at the protein level. Without linkage information between those exons, the fragmental information from individual exons generates incomplete data and is not sufficient for definitive haplotype determination.

Improved methods of HLA typing are of great interest for research and clinical applications.

SUMMARY OF THE INVENTION

Compositions, including primers for amplification, and methods are provided for accurately determining the haplotype of an individual, or for simultaneous determination of haplotypes from a plurality of individuals simultaneously. In some embodiments the haplotype is an HLA Class I haplotype. In other embodiments the haplotype is an HLA Class II haplotype. The information thus provided is useful in screening individuals for transplantation, as well as for the determination of HLA haplotypes associated with various diseases, including a number immune-associated diseases.

The methods of the invention comprise the steps of: amplifying an entire HLA gene, deep sequencing the amplified gene; and performing deconvolution analysis to resolve the haplotype of the gene. The methods of the invention determine the entire genomic region of a particular HLA locus including both intron and exons. The resultant consensus sequences provides linkage information between different exons, and produces the unique sequence from each of the two genes from the individual sample being typed. The sequence information in intron regions along with the exon sequences provides an accurate HLA haplotype, which may be critical to solve incompatibility problems that current HLA haplotyping approaches have thus far failed to address.

In the amplification step, a preferred method is long range polymerase chain reaction. For each HLA gene, multiple sets of gene specific PCR primers, for example as shown in Table 1, and are designed to amplify the genomic area covering the entire HLA gene including all introns and exons in a single reaction. Genes in the HLA families share a high degree of sequence similarity to each other and to pseudogenes in the same region, which similarity is challenging for the specific amplification of a desired gene target. Gene-specific primers are selected from the regions flanking the gene target. Generally a nested PCR amplification is performed, where each target is amplified with two sets of primers—one set internal to the other. The most polymorphic exons and the intervening sequences for each genes are amplified as a single product. The primers are chosen to lie outside of regions of high variability, and if necessary multiple primers are included in a reaction, to ensure amplification of all known alleles for each gene.

Equimolar amounts of the amplified gene products are pooled to ensure equal representation of each gene and may be ligated together to minimize bias in the representation of the ends of the amplified fragments. These ligated products are randomly sheared to an average fragment size of from about 200 to about 700, usually from about 300 to about 600 bp, or from about 400 to about 500 bp in length. In preparation for sequencing, barcodes are ligated to the resulting fragments, where each barcode includes a target specific identifier for the source of the genomic DNA and the gene, and a sequencing adaptor. Sequence runs may range from about 100 to about 500 nucleotides, and may be performed from each end of the fragment. Each sequence can therefore be assigned to the sample and the gene from which it was obtained.

The sequence data is deconvoluted and assigned to each sample, and to each gene using the target specific barcode. Each sequence is read at least about 100 times, and may be read at least about 1000 times, or at least about 10,000 times. Sequence reads for a particular gene will be mapped to its corresponding reference sequence. The novel computational algorithm "Chromatid Sequence Alignment" (CSA) is applied. The CSA algorithm was been designed to use short DNA sequence fragments generated by high-throughput sequencing instruments. This algorithm efficiently clusters sequence fragments properly according to their origins and effectively reconstruct chromatid sequences. The output sequence from CSA algorithm consisting of consecutive nucleotides and covering an entire HLA gene provides us with the information to call haplotype of HLA loci, or any other similarly complex and polymorphic locus.

A report may be prepared disclosing the identification of the haplotypes of the alleles that are sequenced by the methods of the invention, and may be provided to the individual from which the sample is obtained, or to a suitable medical professional.

In some embodiments, a kit is provided comprising a set of primers suitable for amplification of the one or more genes of the HLA locus, e.g. the class I genes: HLA-A, HLA-B, HLA-C; the Class II gene DRB, etc. The primers may be selected from those shown in Table 1. The kit may further comprise reagents for amplification and sequencing. The kit may further comprise instructions for use; and optionally includes software for chromatid sequence alignment.

BRIEF DESCRIPTION OF THE DRAWINGS

FIG. 11 is a schematic of the chromatid sequence alignment.

DETAILED DESCRIPTION OF THE EMBODIMENTS

Figure 1:
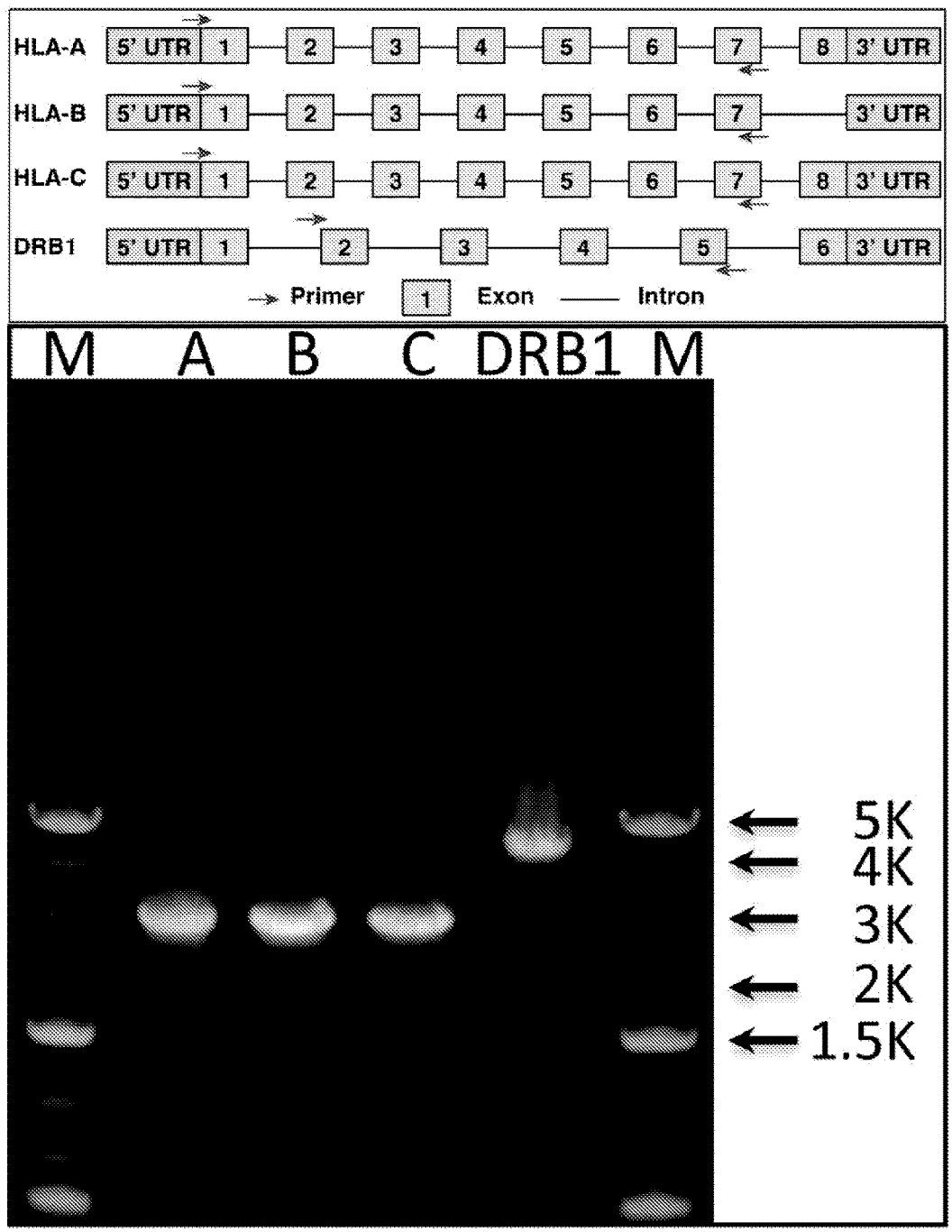
FIG. 1. Location of long-range PCR primers and PCR amplicons in HLA genes. (A) For class I HLA gene (HLA-A, -B, and -C), the forward primer is located in exon 1 near the first codon and the reverse primer is located in exon 7. For HLA-DRB1, the forward primer is located at the boundary between intron 1 and exon 2 and the reverse primer is located within exon 5. Note that the size of exon or intron in the drawing is not proportional to their actual size. (B) Agarose gel (0.8%) showing amplicons from long range PCR. HLA-A, -B, -C amplicons are 2.7 kb in length, and –DRB1 amplicon is around 4.1 kb.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. In this specification and the appended claims, the singular forms "a," "an" and "the" include plural reference unless the context clearly dictates otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, illustrative methods, devices and materials are now described.

All publications mentioned herein are incorporated herein by reference for the purpose of describing and disclosing the subject components of the invention that are described in the publications, which components might be used in connection with the presently described invention.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

DEFINITIONS

An "allele" is one of the different nucleic acid sequences of a gene at a particular locus on a chromosome. One or more genetic differences can constitute an allele. Examples of HLA allele sequences are set out in Mason and Parham (1998) *Tissue Antigens* 51: 417-66, which list HLA-A, HLA-B, and HLA-C alleles and Marsh et al. (1992) *Hum. Immunol.* 35:1, which list HLA Class II alleles for DRA, DRB, DQA1, DQB1, DPA1, and DPB1.

A "locus" is a discrete location on a chromosome that constitutes a gene. Exemplary loci are the class I MHC genes designated HLA-A, HLA-B and HLA-C; nonclassical class I genes including HLA-E, HLA-F, HLA-G, HLA-H, HLA-J and HLA-X, MIC; and class II genes such as HLA-DP, HLA-DQ and HLA-DR.

The MICA (PERB11.1) gene spans a 11 kb stretch of DNA and is approximately 46 kb centromeric to HLA-B. MICB (PERB11.2) is 89 kb farther centromeric to MICA (MICC, MICD and MICE are pseudogenes). Both genes are highly polymorphic at all three alpha domains and show 15-36% sequence similarity to classical class I genes. MIC genes are classified as MHC class Ic genes in the beta block of MHC.

A method of "identifying an HLA genotype" is a method that permits the determination or assignment of one or more genetically distinct HLA genetic polymorphisms.

The term "amplifying" refers to a reaction wherein the template nucleic acid, or portions thereof, are duplicated at least once. Unless specifically stated "amplifying" may refer to arithmetic, logarithmic, or exponential amplification. The amplification of a nucleic acid can take place using any nucleic acid amplification system, both isothermal and thermal gradient based, including but not limited to, polymerase chain reaction (PCR), reverse-transcription-polymerase chain reaction (RT-PCR), ligase chain reaction (LCR), self-sustained sequence reaction (3 SR), and transcription mediated amplifications (TMA). Typical nucleic acid amplification mixtures (e.g. PCR reaction mixture) include a nucleic acid template that is to be amplified, a nucleic acid polymerase, nucleic acid primer sequence(s), and nucleotide triphosphates, and a buffer containing all of the ion species required for the amplification reaction.

An "amplification product" is a single stranded or double stranded DNA or RNA or any other nucleic acid products of isothermal and thermal gradient amplification reactions that include PCR, TMA, 3SR, LCR, etc.

The term "amplicon" is used herein to mean a population of DNA molecules that has been produced by amplification, e.g., by PCR.

The phrase "template nucleic acid" refers to a nucleic acid polymer that is sought to be copied or amplified. The "template nucleic acid(s)" can be isolated or purified from a cell, tissue, animal, etc. Alternatively, the "template nucleic acid(s)" can be contained in a lysate of a cell, tissue, animal, etc. The template nucleic acid can contain genomic DNA, cDNA, plasmid DNA, etc.

An "HLA allele-specific" primer is an oligonucleotide that hybridizes to nucleic acid sequence variations that define or partially define that particular HLA allele.

An "HLA locus-specific" primer is an oligonucleotide that permits the amplification of a HLA locus sequence or that can hybridize specifically to an HLA locus.

A "forward primer" and a "reverse primer" constitute a pair of primers that can bind to a template nucleic acid and under proper amplification conditions produce an amplification product. If the forward primer is binding to the sense strand then the reverse primer is binding to antisense strand. Alternatively, if the forward primer is binding to the antisense strand then the reverse primer is binding to sense strand. In essence, the forward or reverse primer can bind to either strand as long as the other reverse or forward primer binds to the opposite strand.

The phrase "hybridizing" refers to the binding, duplexing, or hybridizing of a molecule only to a particular nucleotide sequence or subsequence through specific binding of two nucleic acids through complementary base pairing. Hybridization typically involves the formation of hydrogen bonds between nucleotides in one nucleic acid and complementary sequences in the second nucleic acid.

The phrase "hybridizing specifically" refers to hybridizing that is carried out under stringent conditions.

The term "stringent conditions" refers to conditions under which a capture oligonucleotide, oligonucleotide or amplification product will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the capture oligonucleotides are occupied at equilibrium). Typically, stringent conditions will be those in which the salt concentration is at most about 0.01 to 1.0 M $Na^+$ ion concentration (or other salts) at pH 7.0 to 8.3 and the temperature is at least about 30° C. for short probes (e.g., 10 to 50 nucleotides). Stringent conditions may also be achieved with the addition of destabilizing agents such as formamide. An extensive guide to the hybridization and washing of nucleic acids is found in Tijssen (1993) *Laboratory Techniques in biochemistry and molecular biology—hybridization with nucleic acid probes parts I and II*, Elsevier, N.Y., and, Choo (ed) (1994) *Methods In Molecular Biology Volume 33—In Situ Hybridization Protocols Humana Press Inc.*, New Jersey; Sambrook et al., *Molecular Cloning, A Laboratory Manual* ($2^{nd}$ ed. 1989); *Current Protocols in Molecular Biology* (Ausubel et al., eds., (1994)).

The term "complementary base pair" refers to a pair of bases (nucleotides) each in a separate nucleic acid in which each base of the pair is hydrogen bonded to the other. A "classical" (Watson-Crick) base pair always contains one purine and one pyrimidine; adenine pairs specifically with thymine (A-T), guanine with cytosine (G-C), uracil with adenine (U-A). The two bases in a classical base pair are said to be complementary to each other.

The term "portions" should similarly be viewed broadly, and would include the case where a "portion" of a DNA strand is in fact the entire strand.

The term "specificity" refers to the proportion of negative test results that are true negative test result. Negative test results include false positives and true negative test results.

The term "sensitivity" is meant to refer to the ability of an analytical method to detect small amounts of analyte. Thus, as used here, a more sensitive method for the detection of amplified DNA, for example, would be better able to detect small amounts of such DNA than would a less sensitive method. "Sensitivity" refers to the proportion of expected results that have a positive test result.

The term "reproducibility" as used herein refers to the general ability of an analytical procedure to give the same result when carried out repeatedly on aliquots of the same sample.

Methods and Compositions

Compositions and methods are provided for accurately determining the haplotype of an individual. The methods include amplifying an entire HLA gene, deep sequencing the amplified gene; and performing deconvolution analysis to resolve the haplotype of the gene. In particular, the methods of the present invention are useful for determining HLA genotypes of samples from subjects. Such genotyping is important in the clinical arena for the diagnosis of disease, transplantation of organs, and bone marrow and cord blood applications.

The samples from which DNA sample is obtained may include any suitable cell source, e.g. blood, saliva, skin, etc., of which blood samples are typically conveniently obtained. Samples may be fresh or frozen, and extracted DNA may be dried or precipitated and stored for long periods of time.

In the amplification step, a preferred method is long range polymerase chain reaction. For each HLA gene, multiple sets of gene specific PCR primers, for example as shown in Table 1, and are designed to amplify the genomic area covering the entire HLA gene including all introns and exons in a single reaction. Genes in the HLA families share a high degree of sequence similarity to each other and to pseudogenes in the same region, which similarity is challenging for the specific amplification of a desired gene target. Gene-specific primers are selected from the regions flanking the gene target. Generally a nested PCR amplification is performed, where each target is amplified with two sets of primers—one set internal to the other. The most polymorphic exons and the intervening sequences for each genes are amplified as a single product. The primers are chosen to lie outside of regions of high variability, and if necessary multiple primers are included in a reaction, to ensure amplification of all known alleles for each gene.

The sequences of many HLA alleles are publicly available through GenBank and other gene databases and have been published. In the design of the HLA primer pairs for the primer mixes, primers are selected based on the known HLA sequences available in the literature. Those of skill in the art will recognize a multitude of oligonucleotide compositions that can be used as HLA target-specific primers.

Equimolar amounts of the amplified gene products are pooled to ensure equal representation of each gene and may be ligated together to minimize bias in the representation of the ends of the amplified fragments. These ligated products are randomly sheared to an average fragment size of from about 200 to about 700, usually from about 300 to about 600 bp, or from about 400 to about 500 bp in length. In preparation for sequencing, barcodes are ligated to the resulting fragments, where each barcode includes a target specific identifier for the source of the genomic DNA and the gene, and a sequencing adaptor. Sequence runs may range from about 100 to about 500 nucleotides, and may be performed from each end of the fragment. Each sequence can therefore be assigned to the sample and the gene from which it was obtained.

Any appropriate sequencing method may be used in the context of the invention. Common methods include sequencing-by-synthesis, Sanger or gel-based sequencing, sequencing-by-hybridization, sequencing-by-ligation, or any other available method. Particularly preferred are high throughput sequencing methods. In some embodiments of the invention, the analysis uses pyrosequencing (e.g., massively parallel pyrosequencing) relying on the detection of pyrophosphate release on nucleotide incorporation, rather than chain termination with dideoxynucleotides, and as described by, for example, Ronaghi et al. (1998) Science 281:363; and Ronaghi et al. (1996) Analytical Biochemistry 242:84, herein specifically incorporated by reference. The pyrosequencing method is based on detecting the activity of DNA polymerase with another chemiluminescent enzyme. Essentially, the method allows sequencing of a single strand of DNA by synthesizing the complementary strand along it, one base pair at a time, and detected which base was actually added at each step. The template DNA is immobile and solutions of selected nucleotides are sequentially added and removed. Light is produced only when the nucleotide solution complements the first unpaired base of the template.

Sequencing platforms that can be used in the present disclosure include but are not limited to: pyrosequencing, sequencing-by-synthesis, single-molecule sequencing, nanopore sequencing, sequencing-by-ligation, or sequencing-by-hybridization. Preferred sequencing platforms are those commercially available from Illumina (RNA-Seq) and Helicos (Digital Gene Expression or "DGE"). "Next generation" sequencing methods include, but are not limited to those commercialized by: 1) 454/Roche Lifesciences including but not limited to the methods and apparatus described in Margulies et al., Nature (2005) 437:376-380 (2005); and U.S. Pat. Nos. 7,244,559; 7,335,762; 7,211,390; 7,244,567; 7,264,929; 7,323,305; 2) Helicos BioSciences Corporation (Cambridge, Mass.) as described in U.S. application Ser. No. 11/167,046, and U.S. Pat. Nos. 7,501,245; 7,491,498; 7,276,720; and in U.S. Patent Application Publication Nos. US20090061439; US20080087826; US20060286566; US20060024711; US20060024678; US20080213770; and US20080103058; 3) Applied Biosystems (e.g. SOLiD sequencing); 4) Dover Systems (e.g., Polonator G.007 sequencing); 5) Illumina as described U.S. Pat. Nos. 5,750, 341; 6,306,597; and 5,969,119; and 6) Pacific Biosciences as described in U.S. Pat. Nos. 7,462,452; 7,476,504; 7,405, 281; 7,170,050; 7,462,468; 7,476,503; 7,315,019; 7,302, 146; 7,313,308; and US Application Publication Nos. US20090029385; US20090068655; US20090024331; and US20080206764. All references are herein incorporated by reference. Such methods and apparatuses are provided here by way of example and are not intended to be limiting.

The sequence data is deconvoluted and assigned to each sample, and to each gene using the target specific barcode. Each sequence is read at least about 100 times, and may be read at least about 1000 times, or at least about 10,000 times. Sequence reads for a particular gene will be mapped to its corresponding reference sequence. The novel computational algorithm "Chromatid Sequence Alignment" (CSA) is applied. The CSA algorithm was been designed to use short DNA sequence fragments generated by high-throughput sequencing instruments. This algorithm efficiently clusters sequence fragments properly according to their origins and effectively reconstruct chromatid sequences. The output sequence from CSA algorithm consisting of consecutive nucleotides and covering an entire HLA gene provides us with the information to call haplotype of HLA loci, or any other similarly complex and polymorphic locus.

When sequence reads are mapped onto a correct reference sequence, they form a continuous tiling pattern over the entire sequenced region. When reads were mapped onto an incorrect reference sequence, they formed a staggered tiling pattern at some positions of the sequenced region. To quantify this difference between the two alignment patterns, the number of "central reads" for any given point is counted, where central reads are empirically defined as mapped reads for which the ratio between the length of the left arm and that of the right arm related to a particular point is between 0.5 and 2. The genotype-calling algorithm is based on the assumption that more reads are mapped to correct reference(s) than to incorrect reference(s). The minimum coverage of overall reads (MCOR) and computed; and the minimum coverage of central reads (MCCR) for each reference is computed. The MCCR values for 30 bases near intron/exon boundaries are ignored, as they are always zero, based on the definition of central reads and the cutoff length. References with an MCOR less than 20 and an MCCR less than 10 are eliminated, as they were unlikely to be correct. From the remaining references, all possible combinations of either one reference (homozygous allele) or two references (heterozygous alleles) of the same locus are enumerated, and the number of distinct reads that mapped to each combination is counted. To compensate for a single reference (homozygous allele), the number of distinct reads is multiplied with an empirical value of 1.05 to avoid miscalls due to spurious alignments. The member(s) in the combination with maximum number of distinct reads is assigned as the genotype of that particular sample.

To ensure that unmapped nucleotides outside aligned regions are taken into consideration, de novo assembly of mapped reads including their unmapped regions is performed. The mapped reads, including unmapped regions, are partitioned into tiled 40-base fragments with a one base offset. A directed weighted graph is built where each distinct fragment is represented as a node and two consecutive fragments of the same read are connected, and an edge between two nodes is weighted with the frequency of reads from the two connected nodes. A contig is constructed on the path with the maximum sum of weights. By comparing a contig with its corresponding reference sequence, differences between a contig built from reads and its closest reference can be identified.

The information obtained from the haplotype analysis may be used to diagnose a condition, for tissue matching, blood typing, and the like.

The invention includes suitable sets of primers for obtaining high throughput sequence information for haplotyping Sequencing can be performed on sets of nucleic acids across many individuals or on multiple loci in a sample obtained from one individual.

Also provided herein are software products tangibly embodied in a machine-readable medium, the software product comprising instructions operable to cause one or more data processing apparatus to perform operations comprising: a) clustering sequence data from a plurality of reads to generate a contig as described above; and b) providing an analysis output on said sequence data. Also provided herein are software products tangibly embodied in a machine-readable medium, the software product comprising instructions operable to cause one or more data processing apparatus to perform operations comprising: storing sequence data and clustering the reads to a chromatid.

information to an individual or for cataloging purposes. The haplotype results and databases thereof may be provided in a variety of media to facilitate their use. "Media" refers to a manufacture that contains the expression repertoire information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc.

As used herein, "a computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

A variety of structural formats for the input and output means can be used to input and output the information in the computer-based systems of the present invention. Such presentation provides a skilled artisan with a ranking of similarities and identifies the degree of similarity contained in the test expression repertoire.

The deconvolution and chromatid sequence assignment analysis may be implemented in hardware or software, or a combination of both. In one embodiment of the invention, a machine-readable storage medium is provided, the medium comprising a data storage material encoded with machine readable data which, when using a machine programmed with instructions for using said data, is capable of displaying any of the datasets and data comparisons of this invention. In some embodiments, the invention is implemented in computer programs executing on programmable computers, comprising a processor, a data storage system (including volatile and non-volatile memory and/or storage elements), at least one input device, and at least one output device. Program code is applied to input data to perform the functions described above and generate output information. The output information is applied to one or more output devices, in known fashion. The computer may be, for example, a personal computer, microcomputer, or workstation of conventional design.

Each program can be implemented in a high level procedural or object oriented programming language to communicate with a computer system. However, the programs can be implemented in assembly or machine language, if desired. In any case, the language may be a compiled or interpreted language. Each such computer program can be stored on a storage media or device (e.g., ROM or magnetic diskette) readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

A variety of structural formats for the input and output means can be used to input and output the information in the computer-based systems of the present invention. One format for an output tests datasets possessing varying degrees of similarity to a trusted repertoire. Such presentation provides a skilled artisan with a ranking of similarities and identifies the degree of similarity contained in the test repertoire.

Further provided herein is a method of storing and/or transmitting, via computer, sequence, and other, data collected by the methods disclosed herein. Any computer or computer accessory including, but not limited to software and storage devices, can be utilized to practice the present invention. Sequence or other data (e.g., immune repertoire analysis results), can be input into a computer by a user either directly or indirectly. Additionally, any of the devices which can be used to sequence DNA or analyze DNA or analyze immune repertoire data can be linked to a computer, such that the data is transferred to a computer and/or computer-compatible storage device. Data can be stored on a computer or suitable storage device (e.g., CD). Data can also be sent from a computer to another computer or data collection point via methods well known in the art (e.g., the internet, ground mail, air mail). Thus, data collected by the methods described herein can be collected at any point or geographical location and sent to any other geographical location.

Reagents and Kits

Also provided are reagents and kits thereof for practicing one or more of the above-described methods. The subject reagents and kits thereof may vary greatly. Reagents of interest include reagents specifically designed for use in production of the above described immune repertoire analysis. For example, reagents can include primer sets for PCR amplification and/or for high throughput sequencing. In some embodiments, a kit is provided comprising a set of primers suitable for amplification of the one or more genes of the HLA locus, e.g. the class I genes: HLA-A, HLA-B, HLA-C; the Class II gene DRB, etc. The primers may be selected from those shown in Table 1.

The kits of the subject invention can include the above described gene specific primer collections. The kits can further include a software package for sequence analysis. The kit may include reagents employed in the various methods, such as primers for generating target nucleic acids, dNTPs and/or rNTPs, which may be either premixed or separate, one or more uniquely labeled dNTPs and/or rNTPs, such as biotinylated or Cy3 or Cy5 tagged dNTPs, gold or silver particles with different scattering spectra, or other post synthesis labeling reagent, such as chemically active derivatives of fluorescent dyes, enzymes, such as reverse transcriptases, DNA polymerases, RNA polymerases, and the like, various buffer mediums, e.g. hybridization and washing buffers, prefabricated probe arrays, labeled probe purification reagents and components, like spin columns, etc., signal generation and detection reagents, e.g. streptavidin-alkaline phosphatase conjugate, chemifluorescent or chemiluminescent substrate, and the like.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed, site. Any convenient means may be present in the kits.

The above-described analytical methods may be embodied as a program of instructions executable by computer to perform the different aspects of the invention. Any of the techniques described above may be performed by means of software components loaded into a computer or other information appliance or digital device. When so enabled, the computer, appliance or device may then perform the above-described techniques to assist the analysis of sets of values associated with a plurality of genes in the manner described above, or for comparing such associated values. The software component may be loaded from a fixed media or accessed through a communication medium such as the internet or other type of computer network. The above features are embodied in one or more computer programs may be performed by one or more computers running such programs.

Software products (or components) may be tangibly embodied in a machine-readable medium, and comprise instructions operable to cause one or more data processing apparatus to perform operations comprising: a) clustering sequence data from a plurality of immunological receptors or fragments thereof; and b) providing a statistical analysis output on said sequence data. Also provided herein are software products (or components) tangibly embodied in a machine-readable medium, and that comprise instructions operable to cause one or more data processing apparatus to perform operations comprising: storing and analyzing sequence data.

EXAMPLES

The following examples are offered by way of illustration and not by way of limitation.

Example 1

Accurate Determination of Haplotype of HLA Loci with Ultra-Deep, Shot-Gun Sequencing Human leukocyte antigen (HLA) genes are the most polymorphic in the human genome. They play a pivotal role in the immune response and have been implicated in numerous human pathologies, especially autoimmunity and infectious diseases. Despite their importance, however, they are rarely characterized comprehensively because of the prohibitive cost of standard technologies and the technical challenges of accurately discriminating between these highly-related genes and their many alleles. Here we demonstrate a novel, high resolution, and cost-effective methodology to type HLA genes by sequencing, that combines the advantage of long-range amplification and the power of high-throughput sequencing platforms. We calibrated our method using 40 reference cell lines for HLA-A, -B, -C, and -DRB1 genes with an overall concordance of 99% (226 out of 229 alleles), and the 3 discordant alleles were subsequently re-analyzed to confirm our results. We also typed 59 clinical samples in one lane of an Illumina HiSeq2000 instrument and identified three novel alleles with insertions and deletions. We have further demonstrated the utility of this method in a clinical setting by typing five clinical samples in an Illumina MiSeq instrument with a five-day turnaround. Overall, this technology has the capacity to deliver low-cost, high-throughput, and accurate HLA typing by multiplexing thousands of samples in a single sequencing run. Furthermore, this approach and can also be extended to include other polymorphic genes that are important in immune responses, or other important functions.

Human leukocyte antigen (HLA) genes encode cell-surface proteins that bind and display fragments of antigens to T lymphocytes. This helps to initiate the adaptive immune response in higher vertebrates and thus is critical to the detection and identification of invading microorganisms. Six of the HLA genes (HLA-A, -B, -C, -DQA1, -DQB1 and -DRB1) are extremely polymorphic and constitute the most important set of markers for matching patients and donors for bone marrow transplantation. Specific HLA alleles have been found to be associated with a number of autoimmune diseases, such as multiple sclerosis, narcolepsy, celiac disease, rheumatoid arthritis and type I diabetes. Alleles have also been noted to be protective in infectious diseases such as HIV, and numerous animal studies have shown that these genes are often the major contributors to disease susceptibility or resistance.

HLA genes are among the most polymorphic in the human genome, and the changes in sequence affect the specificity of antigen presentation and histocompatibility in transplantation. A variety of methodologies have been developed for HLA typing at the protein and nucleic acid level. While earlier HLA typing methods distinguished HLA antigens, modern methods such as sequence-based typing (SBT) determine the nucleotide sequences of HLA genes for higher resolution. However, due to cost and time constraints, HLA sequencing technologies have traditionally focused on the most polymorphic regions encoding the peptide-binding groove that binds to HLA antigens, i.e. exons 2 and 3 for the class I genes, and exon 2 for class II genes. Although the polymorphic regions of HLA genes predominantly cluster within these exons, an increasing number of alleles display polymorphisms in other exons and introns as well. Therefore, typing ambiguities can result from two or more alleles sharing identical sequences in the targeted exons, but differing in the exons that are not sequenced. Resolving these ambiguities is costly and labor-intensive, which makes current SBT methods unsuitable for studies involving even a moderately large group of samples.

Here we demonstrate a novel method targeting a contiguous segment of each of four polymorphic HLA genes (HLA-A, -B, -C and -DRB1), which define the minimal requirements for HLA matching for allogeneic hematopoietic stem cell transplantation (HSCT). Each HLA gene was amplified from genomic DNA in a single long-range polymerase chain reaction spanning the majority of the coding regions and covering most known polymorphic sites. This approach has several advantages. First, more polymorphic sites are sequenced to provide genotyping information of higher definition and the physical linkage between exons can be determined to resolve combination ambiguity. Second, long-range PCR primers can be placed in less polymorphic regions, allowing for improved resolution of genetic differences. Third, exons of the same gene can be amplified in one fragment, thereby decreasing coverage variability. We calibrated this typing method on HLA-A, -B, -C, and -DRB1 genes using 40 reference cell-line samples in the SP reference panel provided by the International Histocompatibility Working Group (IHWG, www.ihwg.org) The overall concordance rate of 99% with previous results and verification of our HLA typing results in the 3 discordant alleles by an independent sequencing technology demonstrate that this low-cost, high-throughput HLA typing protocol provides a high level of reliability. In addition, we tested our method on 59 clinical samples and found three new alleles (two short insertions and one single-base deletion), further illustrating the ability of this method to discover novel alleles.

We designed PCR primers for each gene such that the most polymorphic exons and the intervening sequences could be amplified as a single product. For the class I genes HLAA, -B, and -C, primer sequences were selected to amplify the first seven exons. For HLADRB1, we designed primers to capture exons 2-5 and to avoid amplifying a large (approx. 8 kb) intron between exon 1 and exon 2. Equimolar amounts of the four HLA gene products were pooled to ensure equal representation of each gene and ligated together to minimize bias in the representation of the ends of the amplified fragments. These ligated products were then randomly sheared to an average fragment size of 300-350 bp and prepared for Illumina sequencing, after the addition of unique barcodes to identify the source of genomic DNA for each sample, using encoded sequencing adaptors. Each sequencing adaptor had a seven base barcode between the sequencing primer and the start of the DNA fragment being ligated. The barcodes were designed such that at least three bases differed between any two barcodes. Samples sequenced in the same lane were pooled together in equimolar amounts. The sequences of 150 bases from both ends of each fragment for cell-line samples were determined using the Illumina GAIIx sequencing platform. For clinical samples, the sequences of 100 and 150 bases from both ends of each fragment were determined with the Illumina HiSeq2000 and MiSeq platforms, respectively. For GAIIx sequence reads (counting each paired-end read as 2 independent reads), 91.8% of the sequence reads were parsed and separated according to their barcode tags.

After stripping the barcode tags, 95.5% (approximately 54 million sequence reads) were aligned to genomic reference sequences from the IMGT-HLA database with the NCBI BLASTN program, resulting in an average of 10,600 reads per position (coverage), which was estimated based on the number of reads mapped to genomic reference sequences without filtering. For clinical samples, 97.7% of the sequence reads from the HiSeq2000 instrument were parsed and separated according to their barcode tags. After stripping the barcode tags, 96.7% (around 152 million sequence reads) were aligned to genomic references, resulting in an estimated average of 10,000 reads per position.

Classical HLA genotype assignment. Although genomic DNA was amplified and sequenced in our current approach, the standard genotype-calling algorithm relies mainly on the alignment to cDNA references from the IMGT-HLA database due to the lack of genomic reference sequences. Out of 6398 cDNA reference sequences for HLA-A, -B, -C and -DRB1 genes in the IMGT-HLA database released on Oct. 10, 2011, only 375 (5.8%) of them have genomic sequences. The IMGT-HLA database contains sequences of HLA genes, pseudogenes, and related genes, which allowed us to filter out sequences from pseudogenes or other nonclassical HLA genes, such as HLA-, E, -F, -G, -H, -J, -K, -L, -V, -DRB2, -DRB3, -DRB4, DRB5, -DRB6, -DRB7, -DRB8, and -DRB9. After mapping, the alignments were parsed in the following order: a best-match filter, a mismatch filter, a length filter, and a paired-end filter. The best-match filter only kept alignments with best bit-scores. The mismatch filter eliminated alignments containing either mismatches or gaps. The length filter deleted alignments shorter than 50 bases in length if their corresponding exons were longer than 50 bases. It also removed any alignments shorter than their corresponding exons if those were less than 50 bases in length. Finally, the paired-end filter removed alignments in which references were mapped to only one end of a paired-end read, while at least one reference was mapped to both ends of the paired-end read.

HLA genes share extensive similarities with each other, and many pairs of alleles differ by only a single nucleotide; it is this extreme allelic diversity that has made definitive SBT difficult and subject to misinterpretation. For instance, due to the short read lengths generated using the Illumina platform, it is possible for the same read to map to multiple references. In this study, sequencing was performed in the paired-end format so that the combined specificity of paired-end reads could be used to minimize mis-assignment to an incorrect reference. Also, because of sequence similarities amongst different alleles, combinations of different pairs of alleles could result in a similar pattern of observed nucleotide sequence, based on the fortuitous mixture of sequences.

Figure 2:
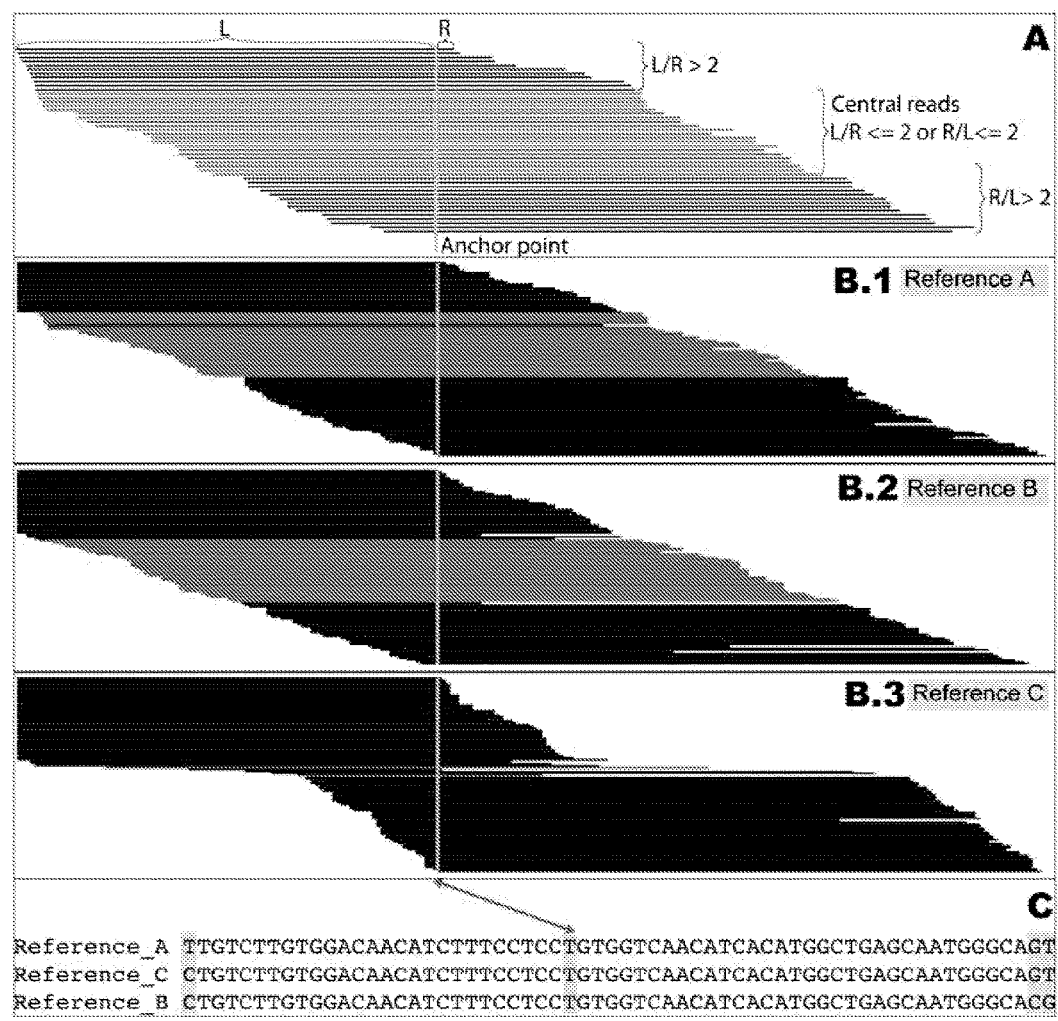
FIG. 2. Mapping patterns of sequencing reads on correct and incorrect references. (A) Central reads of an anchor point are defined as mapped reads, where the ratio between the length of the left arm and that of the right arm related to a particular point is between 0.5 and 2 as those are highlighted in red. (B) Mapping pattern of sequencing reads onto correct references (A and B) and onto an incorrect reference (C). (C) Alignment of references A (SEQ ID NO: 69), B (SEQ ID NO: 71), and C (SEQ ID NO: 70) around the anchor point shown in (B). The anchor points are marked as two double-arrow line.

We noted that when reads were mapped onto a correct reference sequence, they formed a continuous tiling pattern over the entire sequenced region (FIGS. 2B.1 and 2B.2). When reads were mapped onto an incorrect reference sequence, they formed a staggered tiling pattern at some positions of the sequenced region (FIG. 2B.3). To quantify this difference between the two alignment patterns, we counted the number of "central reads" for any given point. Central reads (FIG. 2A) were empirically defined as mapped reads for which the ratio between the length of the left arm and that of the right arm related to a particular point is between 0.5 and 2 (FIG. 2). The genotype-calling algorithm is based on the assumption that more reads are mapped to correct reference(s) than to incorrect reference(s). We could, in a brute-force manner, enumerate all possible combinations of references and count the number of mapped reads for each combination. However, due to the large number of possible combinations, this approach is very inefficient.

Therefore, we applied a heuristic approach to eliminate those implausible references first. We computed the minimum coverage of overall reads (MCOR) and the minimum coverage of central reads (MCCR) for each reference. We ignored the MCCR values for 30 bases near intron/exon boundaries, which were always zero, based on the definition of central reads and the cutoff length (FIG. 2). We eliminated the references with an MCOR less than 20 and an MCCR less than 10, as they were unlikely to be correct. From the remaining references, we enumerated all possible combinations of either one reference (homozygous allele) or two references (heterozygous alleles) of the same locus, and counted the number of distinct reads that mapped to each combination. To compensate for a single reference (homozygous allele), the number of distinct reads was multiplied with an empirical value of 1.05 to avoid miscalls due to spurious alignments. The member(s) in the combination with maximum number of distinct reads were assigned as the genotype of that particular sample. The aforementioned procedure only used the sequence information in the aligned region to do genotype calling. Such a process necessarily introduces bias in the interpretation, since it relies on existing reference data.

However, unmapped nucleotides outside aligned regions could also have important sequence information for new alleles. To ensure that they were taken into consideration, we implemented a program named EZ_assembler which carries out de novo assembly of mapped reads including their unmapped regions. Briefly, we partitioned the mapped reads, including unmapped regions, into tiled 40-base fragments with a one base offset. We built a directed weighted graph where each distinct fragment was represented as a node and two consecutive fragments of the same read were connected, and an edge between two nodes was weighted with the frequency of reads from the two connected nodes. A contig was constructed on the path with the maximum sum of weights. By comparing a contig with its corresponding reference sequence, we were able to identify differences between a contig built from reads and its closest reference. We applied the de novo assembly procedure for each candidate allele to verify the accuracy of the HLA typing, and to detect novel alleles.

Figure 5:
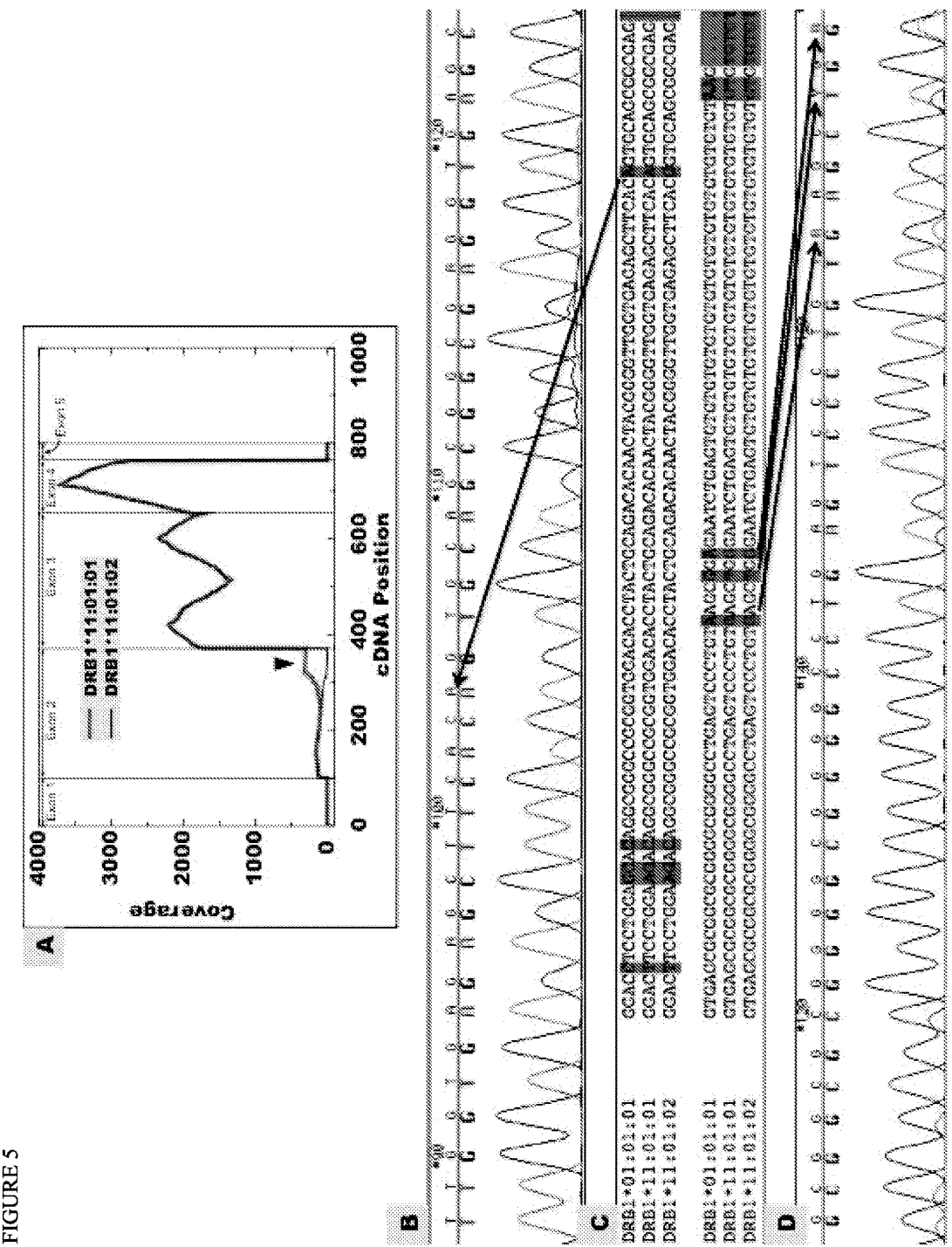
FIG. 5. Sanger sequencing validation of the HLA-DRB1 genotype of the cell-line FH11 (IHW09385). (A) Coverage plots for the reference allele HLA-DRB1 *11:01:02 (blue) and the predicted allele HLA-DRB1 *11:01:01 (red) where the black triangle points to the difference in the coverage plots of these two alleles. (B) Partial Sanger sequencing chromatogram of the amplification products in the exon 2 region of HLA-DRB1 locus. (C) Alignment of HLA-DRB1*01:01:01 (SEQ ID NO: 78), HLA-DRB1*11:01:01 (SEQ ID NO: 79), and HLADRB1* 11:01:02 SEQ ID NO: 80) where the differences among the three alleles are highlighted in red and the intron-exon boundary is indicated in green. (D) Partial Sanger sequencing chromatogram of the amplification products in the intron 2 region of HLA-DRB1 locus. Arrows link positions that are different between the three references in the alignment, and the corresponding positions in the chromatograms. The IMGT-HLA database reports that the HLA-DRB1 locus of FH11 is heterozygous for 01:01:01/11:01:02. Our Illumina data suggest that it should be heterozygous for 01:01:01/11:01:01. The chromatograms in (B) and (D) match the expected pattern of mixture of HLA-DRB1*01:01:01/11:01:01, instead of HLA-DRB1*01:01:01/11:01:02.
Figure 6:
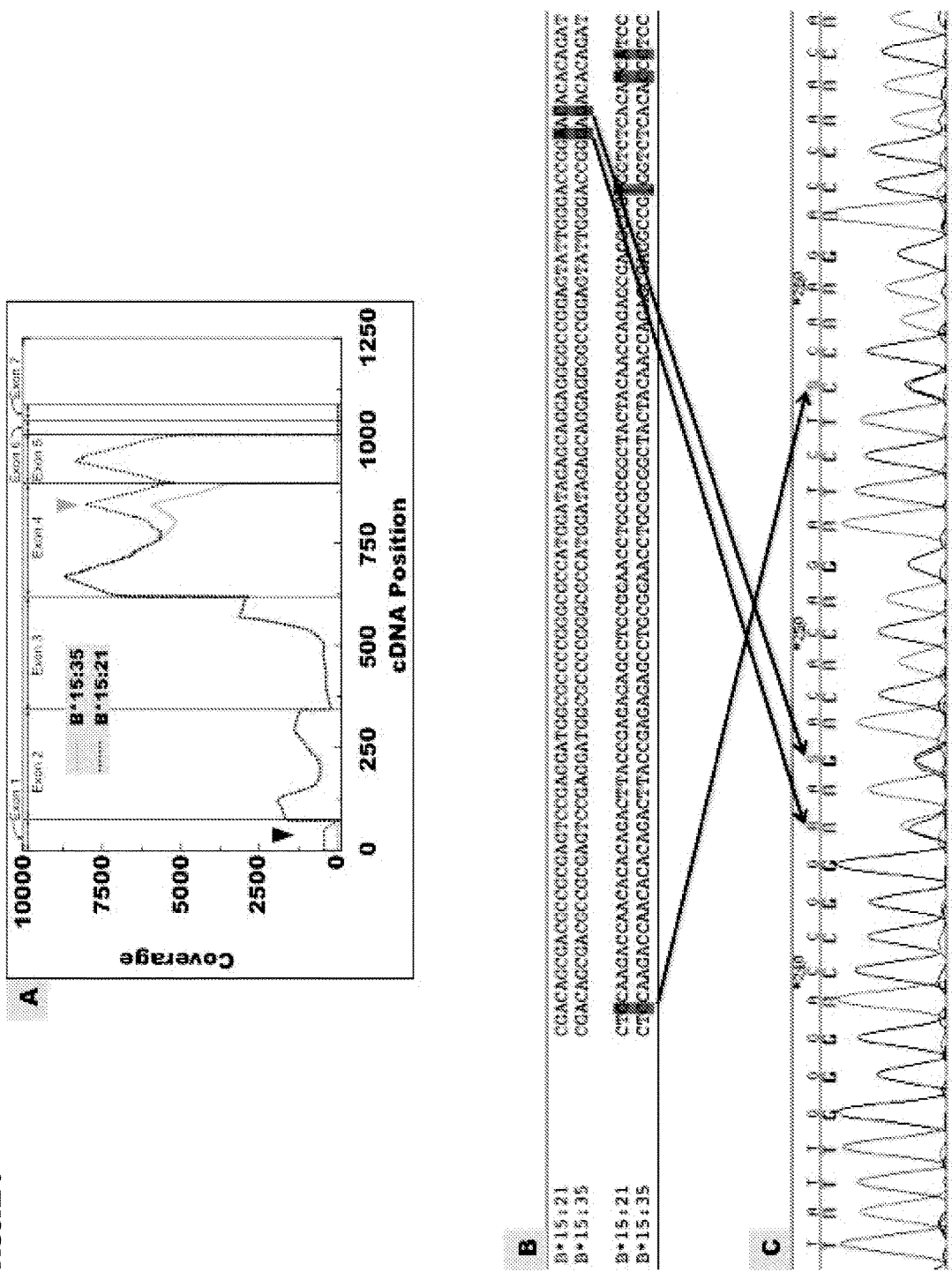
FIG. 6. Sanger sequencing validation of the genotype of HLA-B locus of the cell-line FH34 (IHW09415). A) Coverage plots for the reference allele HLA-B*15:35 (yellow line) and the predicted allele HLA-B*15:21 (black dash line). Note the there is no reference sequence for the HLA-B*15:35 allele in exon 1 region, which is the reason for zero coverage in this region (highlighted by the black triangle). There is no reference sequence for the HLA-B*15: 35 allele in exon 5, 6, 7 either. Although HLA-B*15:21 and HLA-B*15:35 are identical in exon 4, HLA-B*15:35 has lower coverage than HLAB* 15:21 (highlighted in gray triangle) due to removal of reads that did not pass the pair end filter. B) Alignment of HLA-B*15:35 (SEQ ID NO: 82) and HLA-B*15:21 (SEQ ID NO: 81) in partial exon 2 and 3 regions where the differences among the three alleles are highlighted in red and the intron-exon boundary is indicated in green. C) Partial Sanger sequencing chromatogram of the amplification products in the exon 2 region of HLA-B locus. The arrows point out the chromatogram pattern matching the expected pattern of mixture of HLA-B*15:21 and HLA-B*15:35. The reference alleles listed for HLA-B locus of FH34 is 15/15:21 and based on our sequencing data we are able to extend the resolution to 15:21/15:35
Figure 7:
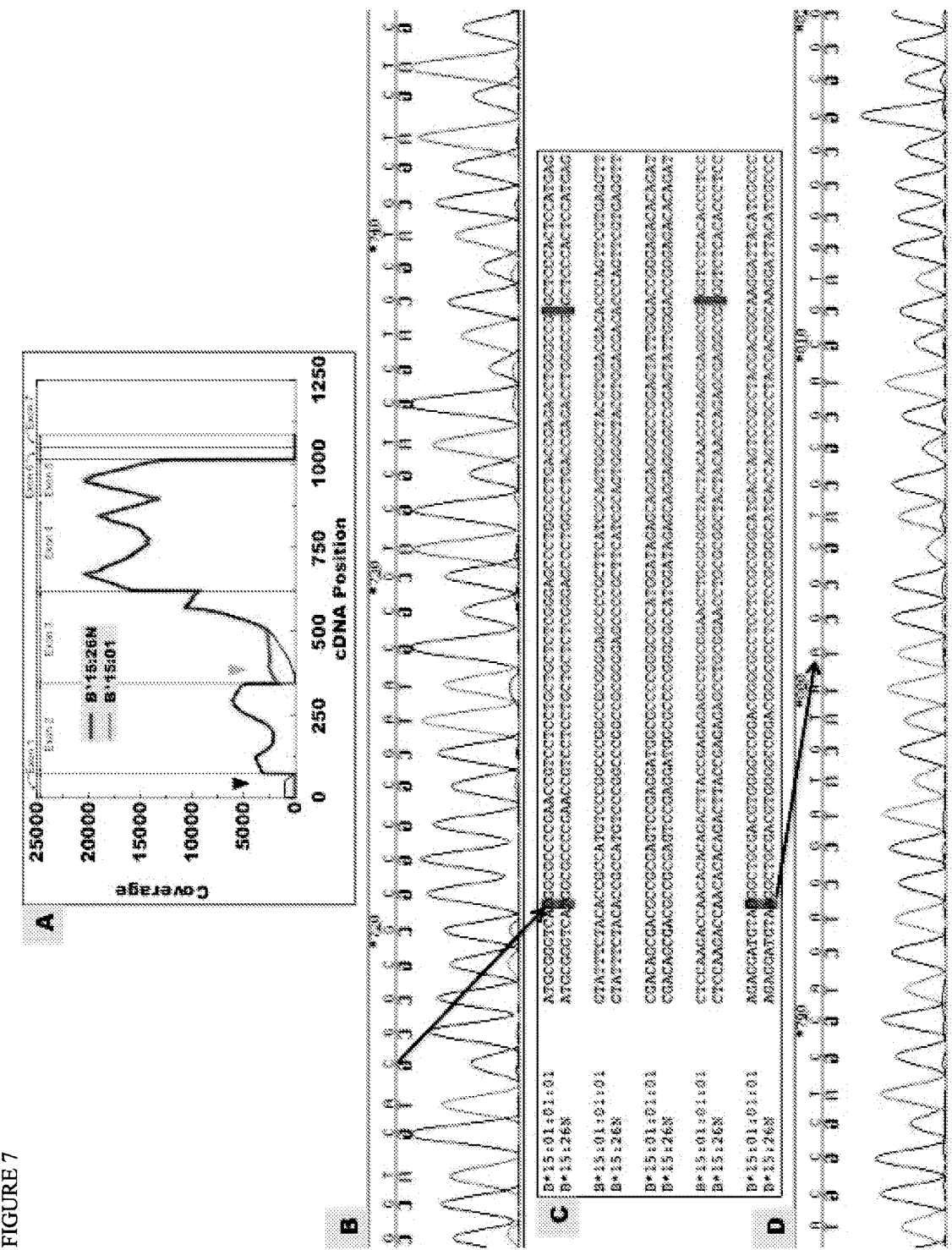
FIG. 7. Sanger sequencing validation of the HLA-B genotype of the cell-line ISH3 (IHW09369). (A) Coverage plots for reference HLA-B*15:26N (red) and HLA-B*15:01 (blue). Reads align continuously onto exons 2, 3, 4, and 5, but not exon 1 of HLAB* 15:26N. There are reads aligning to exon 1 of HLA-B*15:01 (black triangle). (B) Partial Sanger sequencing chromatogram of the amplification products in the exon 1 region of HLA-B locus. The nucleotide in the 11th position of exon 1 is C as in HLAB* 15:01:01. (C) Alignment of HLA-B*15:01:01:01 (SEQ ID NO: 83) and HLA-B*15:26 (SEQ ID NO: 84) where the differences among the three alleles are highlighted in red and the intron-exon boundary is indicated in green. (D) Partial Sanger sequencing chromatogram of the amplification products in the exon 3 region of HLA-B locus. Arrows link positions that are different between the three references in the sequence alignment and the corresponding position in the chromatograms. The IHWG cell-line database reports that the HLA-B locus of ISH3 is homozygous for 15:26N. The chromatograms in panes (B) and (D) suggest that this is a new allele with exon 1 sequence as that of HLA-B*15: 01:01:01 and exons 2, 3, 4, and 5 sequence as that of HLA-B*15:26N. 101 102 103 104 105 0 50 100 150 200 250 300 350 400 450 Minimum Coverage Allele FIG. 8. Minimum coverage (sorted ascending) of all HLA alleles in 59 clinical samples. Only three alleles were typed with minimum coverage less than 100.

Genotyping four highly polymorphic HLA genes in 40 cell-lines. A total of 40 cell-line derived DNA samples of known HLA type were obtained from IHWG and sequenced at four loci (HLA-A, -B, -C, and -DRB1). We compared our predictions with the genotypes reported in the public database for those cell-lines. Out of 229 alleles from the 40 cell-lines typed for HLA-A, -B, -C, and -DRB1 loci, the concordance of our approach with previously determined HLA types was 99% (226/229). To further test the accuracy of our approach, we evaluated these discordant alleles by using an independent long-range PCR amplification, and sequenced the PCR products using Sanger sequencing. The HLA-DRB1 locus in the cell line FH11 (IHW09385) was previously reported as 01:01/11:01:02, which we found to be 01:01/11:01:01. One nucleotide, 12 bases upstream from the end of exon 2, differentiated HLA-DRB1*11:01:01 from HLA-DRB1*11:01:02. Sanger sequencing verified that the HLA-DRB1 locus of the cell-line FH11 is 01:01/11:01:01 (FIG. 5). The reference alleles listed for the HLA-B locus of the cell-line FH34 (IHW09415) are 15/15:21 and based on our sequencing data we are able to extend the resolution to 15:35/15:21. Our data showed that Illumina sequencing reads were aligned to both HLA-B*15:21/15:35 references continuously. HLA-B*15:21 and HLA-B*15:35 were different in 3 positions in exon 2, and 7 positions in exon 3. The Sanger sequencing chromatogram indicated the presence of a mixture in the corresponding positions at exon 2, matching the expected combination of HLA-B*15:21/15:35 (FIG. 6). The HLA-B locus of the cell-line ISH3 (IHW09369) was reported as homozygous for 15:26N in the IHWG cell-line database. Our Illumina sequencing reads mapped to exon 2, 3, 4, and 5, but not exon 1 of the HLA-B*15:26N reference. Instead, the reads mapped to exon 1, 3, 4, and 5, but not exon 2 of the HLAB* 15:01:01:01 reference. There is no reference sequence available where the Illumina reads could tile continuously across the reference sequence. The Sanger sequencing data confirmed that ISH3 HLA-B allele had the exon 1 sequence as that of 15:01:01:01 and the sequence of exons 2, 3, 4, and 5 of 15:26N (FIG. 7). This suggests that either there is an error in the exon 1 region of B*15:26N reference sequence or that this represents yet another new B*15 null allele.

Figure 3:
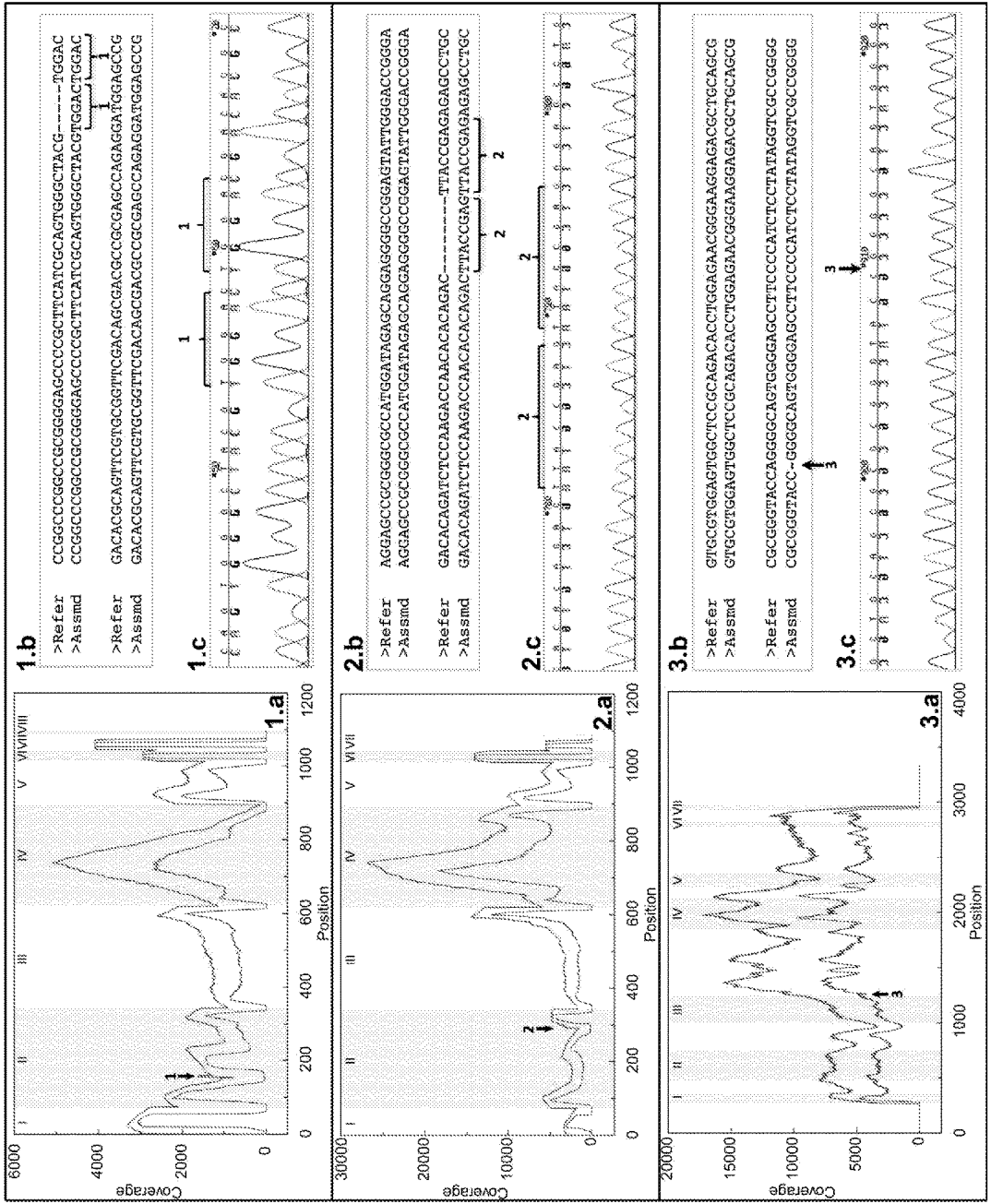
FIG. 3. Identification and verification of three novel alleles with insertions and deletions. (1.a) shows the coverage of overall reads (red) and central reads (blue) mapped onto HLA-A*02:01:01:01 cDNA reference in one clinical sample. (1.b) shows the partial alignment between a contig derived from reads mapped onto HLA-A*02:01:01:01 reference and HLA-A*02:01:01:01 reference. (1.c) shows the chromatogram of Sanger sequence on a clone derived from HLA-A PCR product from the same sample. Black arrows 1 highlight a 5-base 'TGGAC' insertion in coverage plot (1.a), alignment (1.b) ("Refer", SEQ ID NO: 72; "Assmd", SEQ ID NO: 73), and chromatogram (1.c). (2.a) shows the coverage of overall reads (red) and central reads (blue) mapped onto HLA-B*40:02:01 cDNA reference in one clinical sample. (2.b) shows the partial alignment between a contig derived from reads mapped onto HLAB* 40:02:01 reference and HLA-B*40:02:01 reference. (2.c) shows the chromatogram of Sanger sequence on a clone derived from HLA-B PCR product from the same sample. Black arrows 2 highlight an 8-base 'TTACCGAG' insertion in coverage plot (2.a), alignment (2.b) ("Refer" SEQ ID NO: 74; "Assmd" SEQ ID NO: 75), and chromatogram (2.c). (3.a) shows the coverage of overall reads (red) and central reads (blue) mapped onto HLA-B*51:01:01 genomic reference in one clinical sample. (3.b) shows the partial alignment between a contig derived from reads mapped onto HLA-B*51:01:01 reference and HLA-B*51:01:01 reference. (3.c) shows the chromatogram of Sanger sequence on a clone derived from HLA-B PCR product from the same sample. Black arrows 3 highlight a single base 'A' deletion in coverage plot (3.a), alignment (3.b) ("Refer", SEQ ID NO: 76; "Assmd", SEQ ID NO: 77), and chromatogram (3.c). In the coverage plots, exon regions are indicated with Roman numerals.

Genotyping four highly polymorphic HLA genes in 59 clinical samples. To test increased throughput using our approach, we pooled 59 clinical samples and typed HLA-A, -B, -C and -DRB1 in a single HiSeq2000 lane. Of these, 47 samples from an HLA disease association study were typed both by our novel methodology and an oligonucleotide hybridization assay. Even though the resolution of the probe-based assay was lower, the pairwise comparisons of possible genotypes showed overlap in at least one possible genotype for all loci in all samples. There were no allele dropouts in testing by either methodology. Twelve additional samples included specimens of HSCT patients or donors that presented less common or novel allele types (samples 48 to 59). In this group two samples with insertions of 5 and 8 exonic nucleotide insertions were concordantly typed by both classic Sanger sequencing and by the novel methodology described in the present study (FIGS. 3.1 and 3.2). The occurrence of these insertions shows a change in the reading frame with the occurrence of premature termination codons; therefore the corresponding mature HLA proteins of these alleles are not expressed on the cell surface (null). In conventional sequencing, both of heterozygous alleles are co-amplified and sequenced. However, when one of the alleles contains an insertion or deletion, it results in an off-phase heterozygous sequence and the read-out is cumbersome and laborious; in contrast, the read-out obtained by the novel methodology was straightforward.

The precise identification of the type of insertion/deletion in these novel alleles is of crucial importance in clinical histocompatibility practice. The allele containing the insertion or deletion may not be expressed because the reading frame may include changes in the amino acid sequence, resulting in the occurrence of premature termination codons, or it may have altered expression if the mutations are close to mRNA splicing sites (FIG. 3.3). If a mutation of this nature is overlooked, the evaluation of the HLA typing match between a patient and an unrelated donor could easily be incorrect. In the present study we identified the alleles B*40:01:02, A*23:17 and C*07:01:02; which are thought to be rare. But from the data presented here, it is likely that some of them may be the predominant allele of their group (B*40:01:02) or more common than previously thought.

Figure 4:
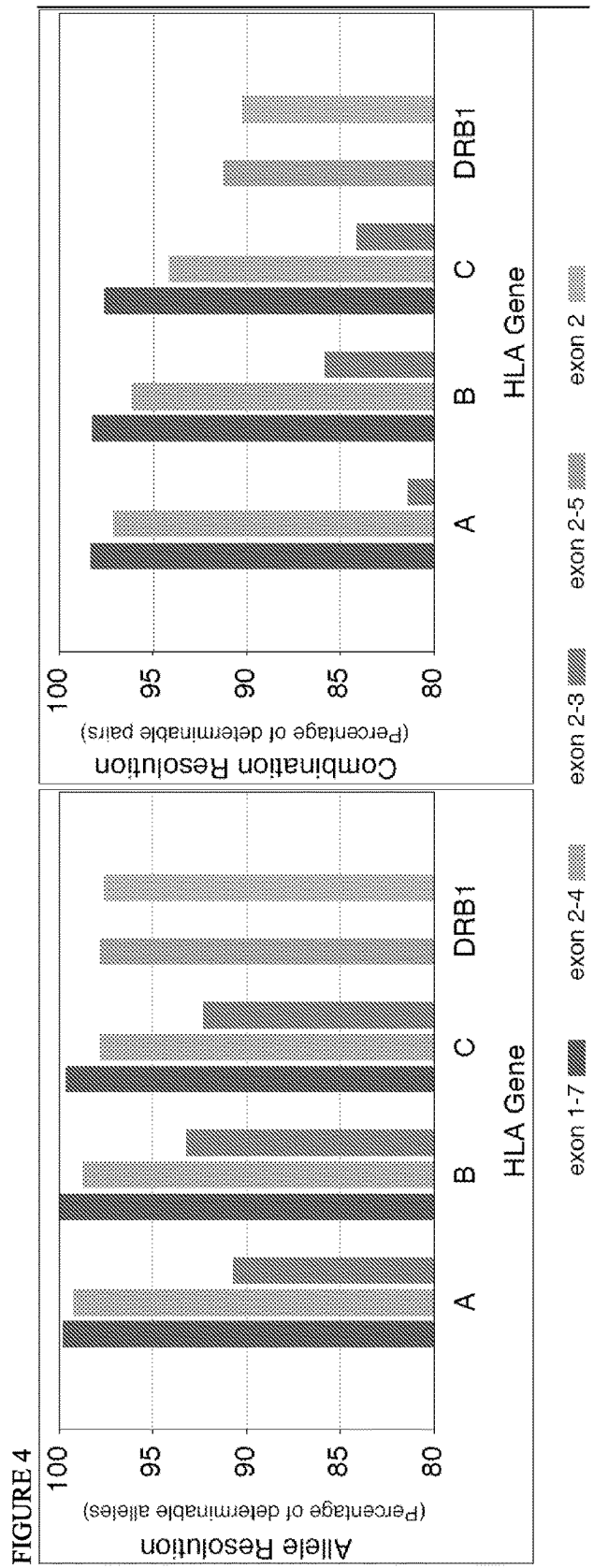
FIG. 4. Comparison of allele resolution (left) and combination resolution (right) if different regions of HLA genes were sequenced. Analysis was based on the IMGT/HLA reference sequence database released on Oct. 10, 2011. The allele resolution is defined as the percentage of alleles that can be resolved definitively when particular regions of a gene are analyzed. The combination resolution is defined as the percentage of combinations of two heterozygous alleles that can be resolved definitively when particular regions of a gene are analyzed. Note that due to the lack of sequence information outside exon 2 for the HLA-DRB1 gene, where only 15% reference sequences cover exon 3 and 7% reference sequences cover exon 4 region for the HLADRB1 gene, the difference between our method and conventional SBT methods over this gene can be estimated accurately.

High-throughput HLA genotyping methodologies using massively parallel sequencing strategies such as Roche/454 sequencing generally amplify separately a few polymorphic exons and sequence in a multiplexed manner. In contrast, the present methods amplify a large genomic region of each gene including introns and the most polymorphic exons in a single PCR reaction and sequenced with a large excess of independent paired-end reads. There are two major ambiguities which arise from conventional SBT methods for HLA genotyping: incomplete-sequencing ambiguities that are commonly seen in typing protocols where alleles vary outside the targeted regions, and combination ambiguities that are frequently encountered where different allele combinations yield the same sequence pattern. As more exons of a gene were sequenced, our method (FIG. 4), which sequenced exons 1 to 7 for HLA class I genes and exons 2 to 5 for HLA-DRB1, substantially enhanced the allele resolution and dramatically improved the combination resolution in comparison to the conventional SBT method, which sequences exons 2 and 3 for HLA class I genes and exon 2 alone for HLA-DRB1. In addition, the extensive sequence coverage allowed us to largely overcome genotype calling artifacts. The paired end sequencing strategy extends the read length effectively to 400-500 bases, which matches that of the Roche/454 platform, while allowing much higher throughput.

The linkage across 400 bases from paired-end reads, together with polymorphic sites in intron regions provided us with important phasing information and was useful to resolve combination ambiguities. We validated this long range PCR amplification and next-generation sequencing approach by re-typing the 40 different IHWG reference cell-lines. The accuracy of this approach was demonstrated with a high-degree (overall 99%) of concordance between our results and those reported in the reference databases. The Sanger sequencing data confirmed our genotype-calling results in the discordant alleles in all cell lines.

Figure 8:
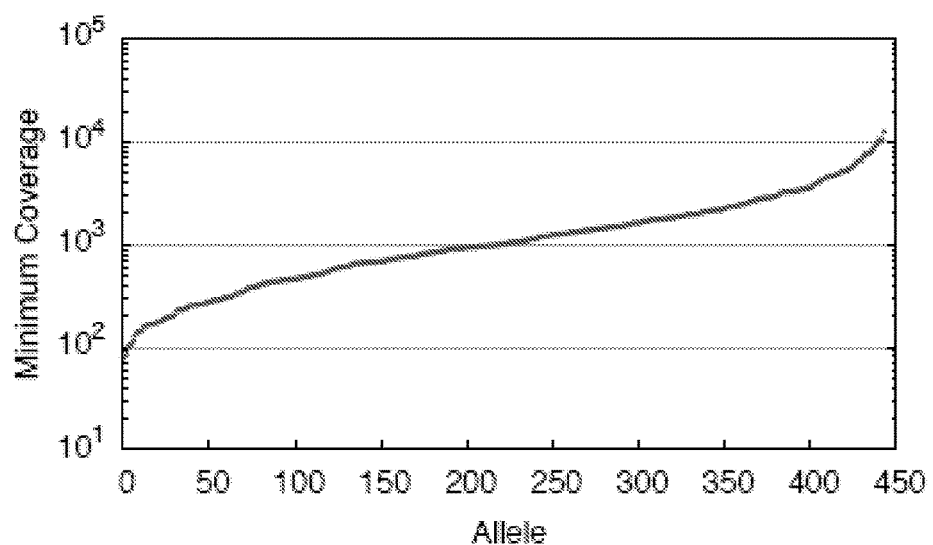
Figure 9:
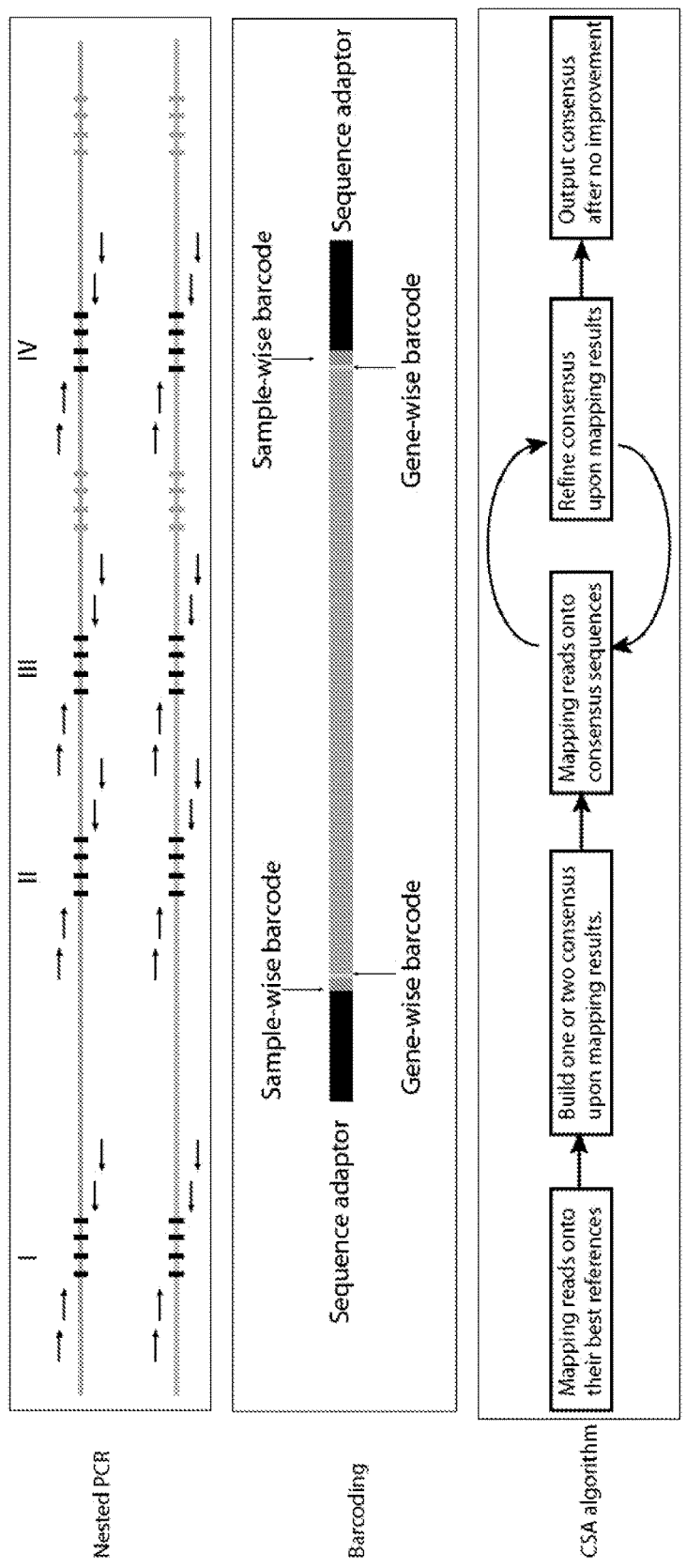
FIG. 9. Schematic diagram of primer selection criteria. 500 bp region was set at both ends of each HLA gene as a cushion region. Primers are chosen from 1500 bp region upstream of forward cushion region and 1500 bp region downstream of the reverse cushion region. Each primer is systematically examined for conservation and specificity. Only those with highest conservation and specificity index (CSI) are picked up.
Figure 10:
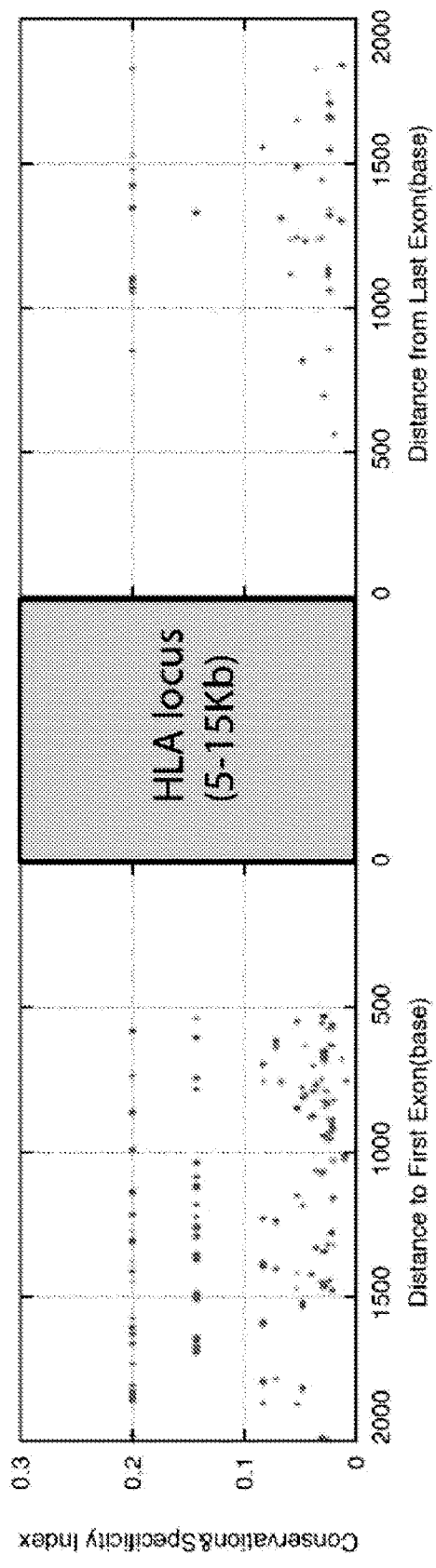
FIG. 10 is a schematic of the HLA locus conservation and specificity.

Although the number of new alleles in public databases has increased dramatically in the past few years, the list is far from being exhaustive as many ethnic groups have yet to be sequenced in depth. Therefore, the ability of a HLA genotyping method to discover new alleles is significant. Our approach demonstrated the ability to identify new alleles that have insertions, deletions, and substitutions. In particular, our strategy of using PCR primers outside polymorphic regions for long-range PCR increases the chance of capturing new alleles. Finally, we were interested in optimizing our approach to accommodate more samples in a single instrument run. Of all alleles from 59 clinical samples typed in a single HiSeq2000 lane, 99.3% of alleles meet the minimum coverage of 100, and the majority of them are beyond 900 (FIG. 8). The ratios of minimum coverage of heterozygous alleles of a gene in the same sample were under four in all but two samples, indicating that heterozygous alleles of the same gene were amplified with similar efficiencies and coverage variation are largely due to pooling unevenness. Our simulation experiment showed that a minimum coverage of 20 could provide reliable information for genotype calling. With an optimized protocol to improve the pooling evenness, we project that for HLA typing 4 genes, we can pool about 180 samples in one lane of Illumina HiSeq2000, or 2700 samples in one HiSeq2000 instrument run (15 lanes), respectively.

In conclusion, we demonstrate here a successful approach for determining accurate HLA genotypes in a high-throughput manner for large numbers of clinical samples simultaneously. Having such a high throughput effectively lowers the cost per sample. Indeed, in the setting of testing many subjects simultaneously, the cost for high resolution typing by the novel methodology is significantly lower than classical Sanger sequencing and it in the same range or lower than the cost of probe-based assays, which have a much lower typing resolution. Therefore, the combination of high-resolution, high-throughput, and low cost will enable comprehensive disease-association studies with large cohorts.

The HLA typing approach described here is useful in obtaining high-resolution HLA results of donors and cord blood units recruited or collected by registries of potential volunteer donors for bone marrow transplantation and cord blood banks. Successful outcomes of allogeneic hematopoietic stem cell transplantation correlate well with close HLA matching between the patient and the selected donor unit. Also, in many diseases early treatment including hematopoietic stem cell transplantation soon after diagnosis, correlates with superior outcomes. Listing donors and units with the corresponding high resolution HLA type can dramatically accelerate the identification of optimally compatible donors.

It is demonstrated here that the methods of the invention can be adapted to accommodate the need for quick turn-around for urgent samples. With the Illumina Miseq, we can type a few samples within 5 days. The typing method can be adapted to suit any sequencing platform, as the alignment algorithms and HLA genotype calling are independent of the sequencing method. The present study shows that the current knowledge of sequence variation in the HLA system can rapidly be expanded by the application of novel nucleotide sequencing technologies.

These data show an ability to analyze, comprehensively, segments of the HLA genes that have not been tested routinely. The testing of these areas gain insight into the fine details of the possible evolutionary pathways of the HLA variation. Furthermore, these methodologies allow refinement of the mapping of susceptibility factors, and of immunity-enabling features. In this regard, the approach can be extended to all HLA genes to discern patient-specific factors that may influence future vaccination strategies. Similarly, we may be able to obtain more precise evaluation of the HLA match grade between patients and unrelated donors in solid organ and hematopoietic stem cell transplantation.
Materials and Methods.

HLA typing reference cell-lines were obtained from the International Histocompatibility Working Group (IHWG) at the Fred Hutchinson Cancer Research Center. The SP reference panel was used for validating the Illumina HLA typing technology. The 47 clinical samples were drawn from the Molecular Genetics of Schizophrenia I linkage sample, which is part of the National Institute of Mental Health Center for Genetic Studies repository program. The other 12 clinical samples were from specimens of HSCT patients or donors that presented less common or novel allele types. Each clinical specimen was collected after subjects signed a written informed consent.

PCR primer design. To design gene-specific primers, we have analyzed all available sequences and chosen primers that would ensure the amplification of all known alleles for each gene. We have avoided regions of high variability, and where necessary, have designed multiple primers to ensure amplification of all alleles. For the class I HLA gene (HLA-A, -B, and -C), the forward primer was located in exon 1 near the first codon, and the reverse primer was located in exon 7. Only a limited number of genomic sequences were available for HLADRB1 genes. Therefore, the PCR primer for HLA-DRB1 genes were placed in less divergent exons. Taking into consideration the size of the PCR amplicons and completeness of genes, the forward primer for HLA-DRB1 was placed at the boundary between intron 1 and exon 2, and the reverse primer within exon 5. To ensure the robustness of the PCR reaction, the first exon of DRB1 was not included in order to avoid amplifying intron 1, which is about 8 kb in length.

Sample preparation. To amplify the selected HLA genes, individual long-range PCR reactions were performed using 5 pmol phosphorylated primers, 100 uM dNTPs, and 2.5 units Crimson LongAmp® Taq DNA Polymerase (New England Biolabs (NEB)) in a 25 µl reaction volume. The reaction included an initial denaturation at 94° C. for 2 min, followed by 40 cycles of 94° C. for 20 sec, 63° C. for 45 sec, and 68° C. for 5 min (for HLA-A, -B, -C) or 7 min for HLA-DRB1. The quality and the molecular weight of each PCR was estimated (assessed) in a 0.8% agarose gel and the approximate amount of each product was estimated by the pixel intensity of the bands. From the amplicon of each gene, approximately 300 ng were pooled and purified using Agencourt AMPure XP beads (Beckman Coulter Genomics,) following the manufacturer's instructions, and subsequently ligated to form concatemers.

For the ligation reaction, overhangs generated by Crimson Taq Polymerase were removed by incubating the reaction with 3 units T4 polymerase (NEB), 2000 units T4 DNA Ligase (NEB) and 1 mM dNTP's in 10×T4 DNA ligase buffer for 10 minutes at room temperature. This was followed by the addition of 1 µl 50% PEG and incubated at room temperature for 30 minutes. Then another 2000 units of T4 DNA Ligase (NEB) was added followed by an overnight incubation at 4° C. After completion of the reaction, 1 µg of ligation product was randomly fragmented in a Covaris E210R (Covaris Inc) DNA shearing instrument to generate 300-350 bp fragments. 225 ng of fragmented DNA was end-repaired using the Quick blunting kit (NEB) followed by addition of deoxyadenosines, using Klenow polymerase, to facilitate addition of barcoded adaptors using 5000 units of Quick Ligase (NEB).

For multiplex processing, multiple samples were pooled together and purified using AMPure XP beads (Beckman Coulter). The samples were run on a Pippin Prep DNA size selection system (Sage Biosciences) to select 350-450 base pair fragments. After elution of the sample, one-half of the eluate was enriched by 13 cycles of PCR using Phusion Hot Start High Fidelity Polymerase (NEB). The enriched libraries were quantified, and the quality checked by an Agilent 2100 Bioanalyzer (Agilent Technologies, Santa Clara, Calif.). The libraries were diluted to a 10 nM concentration using elution buffer, EB (Qiagen). Following denaturation with sodium hydroxide, the amplified libraries were sequenced at a final concentration of 3.5 pM on the Illumina GAIIx instrument (Illumina Inc.) using 8 Illumina 36 cycle SBS sequencing kits (v5) to perform a paired-end, 2×150 bp, run. After sequencing, the resulting images were analyzed with the proprietary Illumina pipeline v1.3 software. Sequencing was done according to the manual from Illumina. To verify discordant calls or potential novel alleles, products from an independent PCR amplification were used to confirm the results by Sanger sequencing using the Big Dye Terminator Kit v3.1 (Life Technologies, Carlsbad, Calif.) and internal sequencing primers. 10 µl of PCR products were digested with 1 unit Shrimp Alkaline Phophatase and 1.0 unit of Exonuclease 1 (Affymetrix Inc.) at 37° C. for 15 min followed by a 20 min heat inactivation at 80° C. The products were directly used in the sequencing reaction or cloned with a TOPO® XL PCR Cloning Kit with One Shot® TOP10 Electrocomp™ E. coli (Invitrogen) prior to sequencing on the 3730 instrument (Life Technologies).

Comparison of Allele Resolution and Combination Resolution when Different Regions were Analyzed Sequence-based typing (SBT) is considered the most comprehensive method for HLA typing. Due to technique difficulty and cost consideration, only the most polymorphic sites of HLA genes were analyzed by this method, which commonly uses the exon 2 and exon 3 sequences for HLA class I analysis and exon 2 alone for HLA class II analysis. With more and more new alleles discovered in the past several years, the accumulated data shown that besides those well-analyzed regions, other regions of HLA genes are polymorphic too. Because of this, IMGT/HLA data has designated new names for each group of HLA alleles that have identical nucleotide sequences across exons encoding the peptide binding domains (exon 2 and 3 for HLA class I and exon 2 for HLA class II) with an upper case 'G' which follows the three-field allele designation of the lowest numbered allele in the group.

To compare the allele resolution, which is defined as the percentage of alleles that can be resolved definitively when particular regions of a gene are analyzed, we counted the number of alleles which do not share the same sequence of the analyzed regions and calculated the percentage of those alleles overall all alleles listed in the IMGT/HLA database, which was released on Oct. 10, 2011. We applied the procedure if exons 1 to 7 (our method), or exons 2, 3, and 4, or exons 2 and 3 (conventional SBT methods) are determined for HLA class I genes, or exons 2 to 5 (our method) or exon 2 (conventional SBT methods) for HLA-DRB1. To compare the combination resolution, which is defined as the percentage of combinations of two heterozygous alleles that can be resolved definitively when particular regions of a gene are analyzed, we first enumerated the combined sequence pattern of the analyzed regions as if two heterozygous alleles were co-amplified and determined by Sanger sequencing method, and counted the number of combinations, each of which has a unique sequence pattern. We then calculated the percentage of those combinations of unique sequence pattern overall all enumerated combinations. We applied the procedure if exons 1 to 7 (our method), or exons 2, 3, and 4, or exons 2 and 3 (conventional SBT methods) are determined for HLA class I genes, or exons 2 to 5 (our method) or exon 2 (conventional SBT methods) for HLA-DRB1. For HLA-DRB1 genes, only 15% and 7% reference sequences cover exon 3 and 4 regions in the IMGT/HLA database released on Oct. 10, 2011. The procedure we employed did not count difference in exon 3 and 4 if there is no sequence information. Therefore, the different between different methods over HLA-DRB1 cannot be clearly illustrated.

| Primers | |
|---|---|
| | direction of the primers 5 prime to 3 prime |
| HLA-A | Forward primers |
| | TCCCCAGACGCCGAGGATGGCC (SEQ ID NO: 1)<br>TCCCCAGACCCCGAGGATGGCC (SEQ ID NO: 2)<br>CCTTGGGGATTCCCCAACTCCGCAG (SEQ ID NO: 3) |
| | Reverse primers |
| | CACATCAGAGCCCTGGGCACTGTC (SEQ ID NO: 4)<br>TTATGCCTACACGAACACAGACACATG (SEQ ID NO: 5) |
| HLA-B | Forward primers |
| | CTCCTCAGACGCCGAGATGCTG (SEQ ID NO: 6)<br>CTCCTCAGACGCCAAGATGCTG (SEQ ID NO: 7)<br>CTCCTCAGACACCGAGATGCTG (SEQ ID NO: 8)<br>CTCCTCAGACGCCGAGATGCGG (SEQ ID NO: 9)<br>CTCCTCAGACGCCAAGATGCGG (SEQ ID NO: 10)<br>CTCCTCAGACACCGAGATGCGG (SEQ ID NO: 11)<br>CCAACTTGTGTCGGGTCCTTCTTCCAGG (SEQ ID NO: 12)<br>CCAACCTATGTCGGGTCCTTCTTCCAGG (SEQ ID NO: 13) |
| | Reverse primers |
| | CACATCAGAGCCCTGGGCACTGTC (SEQ ID NO: 14)<br>CAT CCC TCT TTC TAC AGC AAC CCC CT (SEQ ID NO: 15)<br>CAT CCC TCT TTC GAC AGC AAC CCC CT (SEQ ID NO: 16) |
| HLA-C | Forward primers |
| | CTCCCCAGACGCCGAGATGCGG (SEQ ID NO: 17)<br>CTCCCCAGAGGCCGAGATGCGG (SEQ ID NO: 18)<br>GAGTCCAAGGGGAGAGGTAAGTTTCCT (SEQ ID NO: 19)<br>GAGTCCAAGGGGAGAGGTAAGTGTCCT (SEQ ID NO: 20) |
| | Reverse primers |
| | CTCATCAGAGCCCTGGGCACTGTT (SEQ ID NO: 21)<br>CTA TCC CTC CTC CCA CAC CAA CCG (SEQ ID NO: 22) |
| HLA-DQA | Forward primers |
| | GCTCTTAATACAAACTCTTCAGCTAGTAACT (SEQ ID NO: 23)<br>GCTCTTAATACAAACTCTTCAGCTAGTAACT (SEQ ID NO: 24)<br>GCTCTTAATAGAAACTCTTCAACTAGTAACT (SEQ ID NO: 25) |
| | Reverse primers |
| | TCACAATGGCCCTTGGTGTCT (SEQ ID NO: 26)<br>TCACAATGGCCCCTGGTGTCT (SEQ ID NO: 27)<br>TCACAAGGGCCCTTGGTGTCT (SEQ ID NO: 28) |
| HLA-DQB | Forward primers |
| | CCATCAGGTCCGAGCTGTGTTGACTACCACTT (SEQ ID NO: 29)<br>CCATCAGGTCCGAGCTGTGTTGACTACCACTA (SEQ ID NO: 30)<br>CCATCAGGTCCAAGCTGTGTTGACTACCACTA (SEQ ID NO: 31)<br>CCATCAGGTCTGAGCTGTGTTGACTACCACTA (SEQ ID NO: 32)<br>CCATCAGGTCCGAGCTGTGTTGACTACCACTG (SEQ ID NO: 33) |
| | Reverse primers |
| | CCTAGGGCAGAGCAGGGGGACAAGC (SEQ ID NO: 34)<br>CCTAGGGCAGAGCAGGGAGACAAGC (SEQ ID NO: 35)<br>CCTAGGGCAGAGCAGGGGGACAAGC (SEQ ID NO: 36)<br>AGTCTTGATCCTCATAGCAGCAA (SEQ ID NO: 37) |
| HLA-DPA | Forward primers |
| | ATGCAGCGGACCATGTGTCAACTTATGC (SEQ ID NO: 38) |
| | Reverse primers |
| | ACATTCCCACCTTTACAGTATTTCACAGG (SEQ ID NO: 39) |
| HLA-DPA | Forward primers |
| | CGCCCCCTCCCCGCAGAGAATTA (SEQ ID NO: 40) |
| | Reverse primers |
| | ACCTTTCTTGCTCCTCCTGTGCATGAAG (SEQ ID NO: 41) |
| HLA-DRB | Forward primers |
| | TTCGTGTCCCCACAGCACGTTTC (SEQ ID NO: 42)<br>TTCGTGTACCCGCAGCACGTTTC (SEQ ID NO: 43)<br>TTCGTGTCCCCACAGCATGTTTC (SEQ ID NO: 44)<br>TTCTTGTCCCCCAGCACGTTTC (SEQ ID NO: 45)<br>TTTGTGCCCCACAGCACGTTTC (SEQ ID NO: 46) |
| | Reverse primers |
| | ACCTGTTGGCTGAAGTCCAGAGTGTC (SEQ ID NO: 47)<br>ACCTCTTGGCTGAAGTCCAGAGTGTC (SEQ ID NO: 48)<br>ACCTGTTGGCTGGAAGTCCAGAGTGTC (SEQ ID NO: 49)<br>ACCTGTTGGCGGAAGTCCAGAGTGTC (SEQ ID NO: 50)<br>ACCTGTTGGGTGAAGTCCAGAGTGCC (SEQ ID NO: 51) |
| MIC-A | Forward primers |
| | TGTGCGTTGGGGACAAGGCAATTCT (SEQ ID NO: 52)<br>ACACATCGGAATCACCTAGGGAACT (SEQ ID NO: 53)<br>GGGTAGAAGATGGTAGATGACAGCT (SEQ ID NO: 54)<br>GTGGGGAAAGGACCCCGGTCCCTGC (SEQ ID NO: 55) |
| | Reverse primers |
| | ACCCTTACACTCTCTGCCATGACCA (SEQ ID NO: 56)<br>AAACAGGGCCCAGCCAGGGTCCCTC (SEQ ID NO: 57)<br>GTGCTGTGCAACAGATAATGACTGC (SEQ ID NO: 58)<br>AGGAAGTGAAAAGTGGTCAAGCTGA (SEQ ID NO: 59) |

| Primers | |
|---|---|
| | direction of the primers 5 prime to 3 prime |
| MIC-B | Forward primers |
| | TGCCACCGTCACCACTATCTACTTG (SEQ ID NO: 60) |
| | TACCATCAGGAAGGTTCAAACCATG (SEQ ID NO: 61) |
| | GGTAGAAGATGGTAGGTGATGGCTG (SEQ ID NO: 62) |
| | GAAATGGACACAGTTCCTGATCCTG (SEQ ID NO: 63) |
| | TCTCCCTGAAACCGCTTCTAAATGC (SEQ ID NO: 64) |
| | Reverse primers |
| | GTTGAGGGGAAGCCTTCTCTGTCAC (SEQ ID NO: 65) |
| | CTCCACACCCCTCTCCAGACACTGA (SEQ ID NO: 66) |
| | TTTATGTGGGGAAGGGAAGCCTTTA (SEQ ID NO: 67) |
| | AGTGAATGGGGAAGGAATGAGAGAC (SEQ ID NO: 68) |

HLA A, B, C, DPA & DPB

| Number | Temp. (° C.) | Time (min) | Num. of Cycle |
|---|---|---|---|
| Denaturation | 94 | 3 min | 1 |
| Denaturation | 94 | 30 sec. | 37 |
| Extension | 68 | 6 min | |
| Extension | 68 | 10 min | 1 |
| | 4 | ∞ | 1 |

HLA QA2 & DRB

| | Temperature (° C.) | Time (min) | Cycle |
|---|---|---|---|
| Denaturation | 94 | 3 | 1 |
| Denaturation | 94 | 30 sec | 40 |
| Annealing | 63 | 1 | |
| Extension | 68 | 10 | |
| Final Extension | 68 | 10 | 1 |

HLA QA1 (Red Crimson)

| | Temperature (° C.) | Time (min) | Cycle |
|---|---|---|---|
| Denaturation | 94 | 3 | 1 |
| Denaturation | 94 | 30 sec | 40 |
| Annealing | 63 | 2 | |
| Extension | 68 | 8 | |
| Final Extension | 68 | 10 | 1 |

HLA DQB

| | Temperature (° C.) | Time (min) | Cycle |
|---|---|---|---|
| Denaturation | 94 | 3 | 1 |
| Denaturation | 94 | 30 sec | 40 |
| Annealing | 60 | 2 | |
| Extension | 68 | 8 | |
| Final Extension | 68 | 10 | 1 |

What is claimed is:

1. A method for determining a haplotype of an HLA locus, the method comprising: amplifying an entire HLA gene with nested PCR to amplify a genomic area covering the entire HLA gene including all introns and exons in a single reaction with target-specific primers that hybridize to regions flanking the entire HLA gene; sequencing the amplified gene: and performing deconvolution analysis by chromatid sequence alignment to resolve the haplotype of the locus, wherein the chromatid sequence alignment comprises the steps of: counting "central reads" for any given nucleotide, where central reads are empirically defined as mapped reads for which a ratio between a length of a left arm and that of a right arm related to a particular nucleotide is between 0.5 and 2; computing minimum coverage of overall reads (MCOR) and minimum coverage of central reads (MCCR) for each reference sequence: eliminating references with an MCOR less than 20 and an MCCR less than 10: enumerating all combinations of one reference sequence (homozygous allele) or two reference sequences (heterozygous alleles) of a same locus from the remaining reference sequences; counting distinct reads that map to each combination; wherein member(s) in the combination with maximum number of distinct reads is assigned as a genotype of a sample.

2. The method of claim 1, wherein the primers are selected from those set forth in SEQ ID NO:1-68.

3. The method of claim 1, wherein the amplified gene is fragmented and ligated to barcode oligonucleotides comprising (i) a target specific identifier for a source of the genomic DNA; (ii) a target specific identifier for the gene, and (iii) a sequencing adaptor.

4. The method of claim 3, wherein the fragmented amplified gene is sequenced to a depth of at least 100 reads per sequence.

5. The method of claim 3, wherein the fragmented amplified gene is sequenced to a depth of at least 1000 reads per sequence.

6. The method of claim 1, wherein the locus is an HLA Class I locus.

7. The method of claim 6, wherein the HLA Class I locus includes one or more of HLA-A, HLA-B and HLA-C.

8. The method of claim 1, wherein the locus in an HLA Class II locus.

9. The method of claim 8, wherein the HLA Class II locus is a DR locus.

* * * * *

SEQUENCE LISTING

```
<160> NUMBER OF SEQ ID NOS: 84

<210> SEQ ID NO 1
<211> LENGTH: 22
<212> TYPE: DNA
<213> ORGANISM: Artificial sequence
<220> FEATURE:
<223> OTHER INFORMATION: Synthetic nucleic acid sequence

<400> SEQUENCE: 1
tccccagacg ccgaggatgg cc                                              22

<210> SEQ ID NO 2
<211> LENGTH: 22
<212> TYPE: DNA
<213> ORGANISM: Artificial sequence
<220> FEATURE:
<223> OTHER INFORMATION: Synthetic nucleic acid sequence

<400> SEQUENCE: 2
tccccagacc ccgaggatgg cc                                              22

<210> SEQ ID NO 3
<211> LENGTH: 25
<212> TYPE: DNA
<213> ORGANISM: Artificial sequence
<220> FEATURE:
<223> OTHER INFORMATION: Synthetic nucleic acid sequence
```

```
<400> SEQUENCE: 3
ccttggggat tccccaactc cgcag                                      25

<210> SEQ ID NO 4
<211> LENGTH: 24
<212> TYPE: DNA
<213> ORGANISM: Artificial sequence
<220> FEATURE:
<223> OTHER INFORMATION: Synthetic nucleic acid sequence

<400> SEQUENCE: 4
cacatcagag ccctgggcac tgtc                                       24

<210> SEQ ID NO 5
<211> LENGTH: 27
<212> TYPE: DNA
<213> ORGANISM: Artificial sequence
<220> FEATURE:
<223> OTHER INFORMATION: Synthetic nucleic acid sequence

<400> SEQUENCE: 5
ttatgcctac acgaacacag acacatg                                    27

<210> SEQ ID NO 6
<211> LENGTH: 22
<212> TYPE: DNA
<213> ORGANISM: Artificial sequence
<220> FEATURE:
<223> OTHER INFORMATION: Synthetic nucleic acid sequence

<400> SEQUENCE: 6
ctcctcagac gccgagatgc tg                                         22

<210> SEQ ID NO 7
<211> LENGTH: 22
<212> TYPE: DNA
<213> ORGANISM: Artificial sequence
<220> FEATURE:
<223> OTHER INFORMATION: Synthetic nucleic acid sequence

<400> SEQUENCE: 7
ctcctcagac gccaagatgc tg                                         22

<210> SEQ ID NO 8
<211> LENGTH: 22
<212> TYPE: DNA
<213> ORGANISM: Artificial sequence
<220> FEATURE:
<223> OTHER INFORMATION: Synthetic nucleic acid sequence

<400> SEQUENCE: 8
ctcctcagac accgagatgc tg                                         22

<210> SEQ ID NO 9
<211> LENGTH: 22
<212> TYPE: DNA
<213> ORGANISM: Artificial sequence
<220> FEATURE:
<223> OTHER INFORMATION: Synthetic nucleic acid sequence

<400> SEQUENCE: 9
ctcctcagac gccgagatgc gg                                         22

<210> SEQ ID NO 10
<211> LENGTH: 22
```

```
<212> TYPE: DNA
<213> ORGANISM: Artificial sequence
<220> FEATURE:
<223> OTHER INFORMATION: Synthetic nucleic acid sequence

<400> SEQUENCE: 10
ctcctcagac gccaagatgc gg                                              22

<210> SEQ ID NO 11
<211> LENGTH: 22
<212> TYPE: DNA
<213> ORGANISM: Artificial sequence
<220> FEATURE:
<223> OTHER INFORMATION: Synthetic nucleic acid sequence

<400> SEQUENCE: 11
ctcctcagac accgagatgc gg                                              22

<210> SEQ ID NO 12
<211> LENGTH: 28
<212> TYPE: DNA
<213> ORGANISM: Artificial sequence
<220> FEATURE:
<223> OTHER INFORMATION: Synthetic nucleic acid sequence

<400> SEQUENCE: 12
ccaacttgtg tcgggtcctt cttccagg                                        28

<210> SEQ ID NO 13
<211> LENGTH: 28
<212> TYPE: DNA
<213> ORGANISM: Artificial sequence
<220> FEATURE:
<223> OTHER INFORMATION: Synthetic nucleic acid sequence

<400> SEQUENCE: 13
ccaacctatg tcgggtcctt cttccagg                                        28

<210> SEQ ID NO 14
<211> LENGTH: 24
<212> TYPE: DNA
<213> ORGANISM: Artificial sequence
<220> FEATURE:
<223> OTHER INFORMATION: Synthetic nucleic acid sequence

<400> SEQUENCE: 14
cacatcagag ccctgggcac tgtc                                            24

<210> SEQ ID NO 15
<211> LENGTH: 26
<212> TYPE: DNA
<213> ORGANISM: Artificial sequence
<220> FEATURE:
<223> OTHER INFORMATION: Synthetic nucleic acid sequence

<400> SEQUENCE: 15
catccctctt tctacagcaa cccccct                                         26

<210> SEQ ID NO 16
<211> LENGTH: 26
<212> TYPE: DNA
<213> ORGANISM: Artificial sequence
<220> FEATURE:
<223> OTHER INFORMATION: Synthetic nucleic acid sequence

<400> SEQUENCE: 16
```
catccctctt tcgacagcaa cccccct                                            26

<210> SEQ ID NO 17
<211> LENGTH: 22
<212> TYPE: DNA
<213> ORGANISM: Artificial sequence
<220> FEATURE:
<223> OTHER INFORMATION: Synthetic nucleic acid sequence

<400> SEQUENCE: 17
ctccccagac gccgagatgc gg                                                 22

<210> SEQ ID NO 18
<211> LENGTH: 22
<212> TYPE: DNA
<213> ORGANISM: Artificial sequence
<220> FEATURE:
<223> OTHER INFORMATION: Synthetic nucleic acid sequence

<400> SEQUENCE: 18
ctccccagag gccgagatgc gg                                                 22

<210> SEQ ID NO 19
<211> LENGTH: 27
<212> TYPE: DNA
<213> ORGANISM: Artificial sequence
<220> FEATURE:
<223> OTHER INFORMATION: Synthetic nucleic acid sequence

<400> SEQUENCE: 19
gagtccaagg ggagaggtaa gtttcct                                            27

<210> SEQ ID NO 20
<211> LENGTH: 27
<212> TYPE: DNA
<213> ORGANISM: Artificial sequence
<220> FEATURE:
<223> OTHER INFORMATION: Synthetic nucleic acid sequence

<400> SEQUENCE: 20
gagtccaagg ggagaggtaa gtgtcct                                            27

<210> SEQ ID NO 21
<211> LENGTH: 24
<212> TYPE: DNA
<213> ORGANISM: Artificial sequence
<220> FEATURE:
<223> OTHER INFORMATION: Synthetic nucleic acid sequence

<400> SEQUENCE: 21
ctcatcagag ccctgggcac tgtt                                               24

<210> SEQ ID NO 22
<211> LENGTH: 24
<212> TYPE: DNA
<213> ORGANISM: Artificial sequence
<220> FEATURE:
<223> OTHER INFORMATION: Synthetic nucleic acid sequence

<400> SEQUENCE: 22
ctatccctcc tcccacacca accg                                               24

<210> SEQ ID NO 23
<211> LENGTH: 31
<212> TYPE: DNA
<213> ORGANISM: Artificial sequence

```
<220> FEATURE:
<223> OTHER INFORMATION: Synthetic nucleic acid sequence

<400> SEQUENCE: 23
gctcttaata caaactcttc agctagtaac t                                31

<210> SEQ ID NO 24
<211> LENGTH: 31
<212> TYPE: DNA
<213> ORGANISM: Artificial sequence
<220> FEATURE:
<223> OTHER INFORMATION: Synthetic nucleic acid sequence

<400> SEQUENCE: 24
gctcttaata caaactcttc agctagtaac t                                31

<210> SEQ ID NO 25
<211> LENGTH: 31
<212> TYPE: DNA
<213> ORGANISM: Artificial sequence
<220> FEATURE:
<223> OTHER INFORMATION: Synthetic nucleic acid sequence

<400> SEQUENCE: 25
gctcttaata gaaactcttc aactagtaac t                                31

<210> SEQ ID NO 26
<211> LENGTH: 21
<212> TYPE: DNA
<213> ORGANISM: Artificial sequence
<220> FEATURE:
<223> OTHER INFORMATION: Synthetic nucleic acid sequence

<400> SEQUENCE: 26
tcacaatggc ccttggtgtc t                                           21

<210> SEQ ID NO 27
<211> LENGTH: 21
<212> TYPE: DNA
<213> ORGANISM: Artificial sequence
<220> FEATURE:
<223> OTHER INFORMATION: Synthetic nucleic acid sequence

<400> SEQUENCE: 27
tcacaatggc ccctggtgtc t                                           21

<210> SEQ ID NO 28
<211> LENGTH: 21
<212> TYPE: DNA
<213> ORGANISM: Artificial sequence
<220> FEATURE:
<223> OTHER INFORMATION: Synthetic nucleic acid sequence

<400> SEQUENCE: 28
tcacaagggc ccttggtgtc t                                           21

<210> SEQ ID NO 29
<211> LENGTH: 32
<212> TYPE: DNA
<213> ORGANISM: Artificial sequence
<220> FEATURE:
<223> OTHER INFORMATION: Synthetic nucleic acid sequence

<400> SEQUENCE: 29
ccatcaggtc cgagctgtgt tgactaccac tt                               32
```

<210> SEQ ID NO 30
<211> LENGTH: 32
<212> TYPE: DNA
<213> ORGANISM: Artificial sequence
<220> FEATURE:
<223> OTHER INFORMATION: Synthetic nucleic acid sequence

<400> SEQUENCE: 30
ccatcaggtc cgagctgtgt tgactaccac ta          32

<210> SEQ ID NO 31
<211> LENGTH: 32
<212> TYPE: DNA
<213> ORGANISM: Artificial sequence
<220> FEATURE:
<223> OTHER INFORMATION: Synthetic nucleic acid sequence

<400> SEQUENCE: 31
ccatcaggtc caagctgtgt tgactaccac ta          32

<210> SEQ ID NO 32
<211> LENGTH: 32
<212> TYPE: DNA
<213> ORGANISM: Artificial sequence
<220> FEATURE:
<223> OTHER INFORMATION: Synthetic nucleic acid sequence

<400> SEQUENCE: 32
ccatcaggtc tgagctgtgt tgactaccac ta          32

<210> SEQ ID NO 33
<211> LENGTH: 32
<212> TYPE: DNA
<213> ORGANISM: Artificial sequence
<220> FEATURE:
<223> OTHER INFORMATION: Synthetic nucleic acid sequence

<400> SEQUENCE: 33
ccatcaggtc cgagctgtgt tgactaccac tg          32

<210> SEQ ID NO 34
<211> LENGTH: 25
<212> TYPE: DNA
<213> ORGANISM: Artificial sequence
<220> FEATURE:
<223> OTHER INFORMATION: Synthetic nucleic acid sequence

<400> SEQUENCE: 34
cctagggcag agcaggggga caagc          25

<210> SEQ ID NO 35
<211> LENGTH: 25
<212> TYPE: DNA
<213> ORGANISM: Artificial sequence
<220> FEATURE:
<223> OTHER INFORMATION: Synthetic nucleic acid sequence

<400> SEQUENCE: 35
cctagggcag agcagggaga caagc          25

<210> SEQ ID NO 36
<211> LENGTH: 25
<212> TYPE: DNA
<213> ORGANISM: Artificial sequence
<220> FEATURE:
<223> OTHER INFORMATION: Synthetic nucleic acid sequence

<400> SEQUENCE: 36
cctagggcag agcaggggga caagc              25

<210> SEQ ID NO 37
<211> LENGTH: 23
<212> TYPE: DNA
<213> ORGANISM: Artificial sequence
<220> FEATURE:
<223> OTHER INFORMATION: Synthetic nucleic acid sequence

<400> SEQUENCE: 37
agtcttgatc ctcatagcag caa              23

<210> SEQ ID NO 38
<211> LENGTH: 28
<212> TYPE: DNA
<213> ORGANISM: Artificial sequence
<220> FEATURE:
<223> OTHER INFORMATION: Synthetic nucleic acid sequence

<400> SEQUENCE: 38
atgcagcgga ccatgtgtca acttatgc              28

<210> SEQ ID NO 39
<211> LENGTH: 29
<212> TYPE: DNA
<213> ORGANISM: Artificial sequence
<220> FEATURE:
<223> OTHER INFORMATION: Synthetic nucleic acid sequence

<400> SEQUENCE: 39
acattcccac ctttacagta tttcacagg              29

<210> SEQ ID NO 40
<211> LENGTH: 23
<212> TYPE: DNA
<213> ORGANISM: Artificial sequence
<220> FEATURE:
<223> OTHER INFORMATION: Synthetic nucleic acid sequence

<400> SEQUENCE: 40
cgccccctcc ccgcagagaa tta              23

<210> SEQ ID NO 41
<211> LENGTH: 28
<212> TYPE: DNA
<213> ORGANISM: Artificial sequence
<220> FEATURE:
<223> OTHER INFORMATION: Synthetic nucleic acid sequence

<400> SEQUENCE: 41
acctttcttg ctcctcctgt gcatgaag              28

<210> SEQ ID NO 42
<211> LENGTH: 23
<212> TYPE: DNA
<213> ORGANISM: Artificial sequence
<220> FEATURE:
<223> OTHER INFORMATION: Synthetic nucleic acid sequence

<400> SEQUENCE: 42
ttcgtgtccc cacagcacgt ttc              23

<210> SEQ ID NO 43

-continued

```
<211> LENGTH: 23
<212> TYPE: DNA
<213> ORGANISM: Artificial sequence
<220> FEATURE:
<223> OTHER INFORMATION: Synthetic nucleic acid sequence

<400> SEQUENCE: 43
ttcgtgtacc cgcagcacgt ttc                                            23

<210> SEQ ID NO 44
<211> LENGTH: 23
<212> TYPE: DNA
<213> ORGANISM: Artificial sequence
<220> FEATURE:
<223> OTHER INFORMATION: Synthetic nucleic acid sequence

<400> SEQUENCE: 44
ttcgtgtccc cacagcatgt ttc                                            23

<210> SEQ ID NO 45
<211> LENGTH: 23
<212> TYPE: DNA
<213> ORGANISM: Artificial sequence
<220> FEATURE:
<223> OTHER INFORMATION: Synthetic nucleic acid sequence

<400> SEQUENCE: 45
ttcttgtccc cccagcacgt ttc                                            23

<210> SEQ ID NO 46
<211> LENGTH: 23
<212> TYPE: DNA
<213> ORGANISM: Artificial sequence
<220> FEATURE:
<223> OTHER INFORMATION: Synthetic nucleic acid sequence

<400> SEQUENCE: 46
tttgtgcccc cacagcacgt ttc                                            23

<210> SEQ ID NO 47
<211> LENGTH: 26
<212> TYPE: DNA
<213> ORGANISM: Artificial sequence
<220> FEATURE:
<223> OTHER INFORMATION: Synthetic nucleic acid sequence

<400> SEQUENCE: 47
acctgttggc tgaagtccag agtgtc                                         26

<210> SEQ ID NO 48
<211> LENGTH: 26
<212> TYPE: DNA
<213> ORGANISM: Artificial sequence
<220> FEATURE:
<223> OTHER INFORMATION: Synthetic nucleic acid sequence

<400> SEQUENCE: 48
acctcttggc tgaagtccag agtgtc                                         26

<210> SEQ ID NO 49
<211> LENGTH: 26
<212> TYPE: DNA
<213> ORGANISM: Artificial sequence
<220> FEATURE:
<223> OTHER INFORMATION: Synthetic nucleic acid sequence

<400> SEQUENCE: 49
```

```
acctgttggc tggagtccag agtgtc                                         26

<210> SEQ ID NO 50
<211> LENGTH: 26
<212> TYPE: DNA
<213> ORGANISM: Artificial sequence
<220> FEATURE:
<223> OTHER INFORMATION: Synthetic nucleic acid sequence

<400> SEQUENCE: 50
acctgttggc ggaagtccag agtgtc                                         26

<210> SEQ ID NO 51
<211> LENGTH: 26
<212> TYPE: DNA
<213> ORGANISM: Artificial sequence
<220> FEATURE:
<223> OTHER INFORMATION: Synthetic nucleic acid sequence

<400> SEQUENCE: 51
acctgttggg tgaagtccag agtgcc                                         26

<210> SEQ ID NO 52
<211> LENGTH: 25
<212> TYPE: DNA
<213> ORGANISM: Artificial sequence
<220> FEATURE:
<223> OTHER INFORMATION: Synthetic nucleic acid sequence

<400> SEQUENCE: 52
tgtgcgttgg ggacaaggca attct                                          25

<210> SEQ ID NO 53
<211> LENGTH: 25
<212> TYPE: DNA
<213> ORGANISM: Artificial sequence
<220> FEATURE:
<223> OTHER INFORMATION: Synthetic nucleic acid sequence

<400> SEQUENCE: 53
acacatcgga atcacctagg gaact                                          25

<210> SEQ ID NO 54
<211> LENGTH: 25
<212> TYPE: DNA
<213> ORGANISM: Artificial sequence
<220> FEATURE:
<223> OTHER INFORMATION: Synthetic nucleic acid sequence

<400> SEQUENCE: 54
gggtagaaga tggtagatga cagct                                          25

<210> SEQ ID NO 55
<211> LENGTH: 25
<212> TYPE: DNA
<213> ORGANISM: Artificial sequence
<220> FEATURE:
<223> OTHER INFORMATION: Synthetic nucleic acid sequence

<400> SEQUENCE: 55
gtggggaaag gaccccggtc cctgc                                          25

<210> SEQ ID NO 56
<211> LENGTH: 25
<212> TYPE: DNA
```

<210> SEQ ID NO 57
<211> LENGTH: 25
<212> TYPE: DNA
<213> ORGANISM: Artificial sequence
<220> FEATURE:
<223> OTHER INFORMATION: Synthetic nucleic acid sequence

<400> SEQUENCE: 56
acccttacac tctctgccat gacca 25

<210> SEQ ID NO 57
<211> LENGTH: 25
<212> TYPE: DNA
<213> ORGANISM: Artificial sequence
<220> FEATURE:
<223> OTHER INFORMATION: Synthetic nucleic acid sequence

<400> SEQUENCE: 57
aaacagggcc cagccagggt ccctc 25

<210> SEQ ID NO 58
<211> LENGTH: 25
<212> TYPE: DNA
<213> ORGANISM: Artificial sequence
<220> FEATURE:
<223> OTHER INFORMATION: Synthetic nucleic acid sequence

<400> SEQUENCE: 58
gtgctgtgca acagataatg actgc 25

<210> SEQ ID NO 59
<211> LENGTH: 25
<212> TYPE: DNA
<213> ORGANISM: Artificial sequence
<220> FEATURE:
<223> OTHER INFORMATION: Synthetic nucleic acid sequence

<400> SEQUENCE: 59
aggaagtgaa aagtggtcaa gctga 25

<210> SEQ ID NO 60
<211> LENGTH: 25
<212> TYPE: DNA
<213> ORGANISM: Artificial sequence
<220> FEATURE:
<223> OTHER INFORMATION: Synthetic nucleic acid sequence

<400> SEQUENCE: 60
tgccaccgtc accactatct acttg 25

<210> SEQ ID NO 61
<211> LENGTH: 25
<212> TYPE: DNA
<213> ORGANISM: Artificial sequence
<220> FEATURE:
<223> OTHER INFORMATION: Synthetic nucleic acid sequence

<400> SEQUENCE: 61
taccatcagg aaggttcaaa ccatg 25

<210> SEQ ID NO 62
<211> LENGTH: 25
<212> TYPE: DNA
<213> ORGANISM: Artificial sequence
<220> FEATURE:
<223> OTHER INFORMATION: Synthetic nucleic acid sequence

<400> SEQUENCE: 62
ggtagaagat ggtaggtgat ggctg 25

<210> SEQ ID NO 63
<211> LENGTH: 25
<212> TYPE: DNA
<213> ORGANISM: Artificial sequence
<220> FEATURE:
<223> OTHER INFORMATION: Synthetic nucleic acid sequence

<400> SEQUENCE: 63
gaaatggaca cagttcctga tcctg                                          25

<210> SEQ ID NO 64
<211> LENGTH: 25
<212> TYPE: DNA
<213> ORGANISM: Artificial sequence
<220> FEATURE:
<223> OTHER INFORMATION: Synthetic nucleic acid sequence

<400> SEQUENCE: 64
tctccctgaa accgcttcta aatgc                                          25

<210> SEQ ID NO 65
<211> LENGTH: 25
<212> TYPE: DNA
<213> ORGANISM: Artificial sequence
<220> FEATURE:
<223> OTHER INFORMATION: Synthetic nucleic acid sequence

<400> SEQUENCE: 65
gttgagggga agccttctct gtcac                                          25

<210> SEQ ID NO 66
<211> LENGTH: 25
<212> TYPE: DNA
<213> ORGANISM: Artificial sequence
<220> FEATURE:
<223> OTHER INFORMATION: Synthetic nucleic acid sequence

<400> SEQUENCE: 66
ctccacaccc ctctccagac actga                                          25

<210> SEQ ID NO 67
<211> LENGTH: 25
<212> TYPE: DNA
<213> ORGANISM: Artificial sequence
<220> FEATURE:
<223> OTHER INFORMATION: Synthetic nucleic acid sequence

<400> SEQUENCE: 67
tttatgtggg gaagggaagc cttta                                          25

<210> SEQ ID NO 68
<211> LENGTH: 25
<212> TYPE: DNA
<213> ORGANISM: Artificial sequence
<220> FEATURE:
<223> OTHER INFORMATION: Synthetic nucleic acid sequence

<400> SEQUENCE: 68
agtgaatggg gaaggaatga gagac                                          25

<210> SEQ ID NO 69
<211> LENGTH: 62
<212> TYPE: DNA
<213> ORGANISM: Artificial sequence
<220> FEATURE:

<223> OTHER INFORMATION: Synthetic nucleic acid sequence

<400> SEQUENCE: 69
ttgtcttgtg acaacatct ttcctcctgt ggtcaacatc acatggctga gcaatgggca    60
gt    62

<210> SEQ ID NO 70
<211> LENGTH: 62
<212> TYPE: DNA
<213> ORGANISM: Artificial sequence
<220> FEATURE:
<223> OTHER INFORMATION: Synthetic nucleic acid sequence

<400> SEQUENCE: 70
ctgtcttgtg acaacatct ttcctcctgt ggtcaacatc acatggctga gcaatgggca    60
gt    62

<210> SEQ ID NO 71
<211> LENGTH: 62
<212> TYPE: DNA
<213> ORGANISM: Artificial sequence
<220> FEATURE:
<223> OTHER INFORMATION: Synthetic nucleic acid sequence

<400> SEQUENCE: 71
ctgtcttgtg acaacatct ttcctcctgt ggtcaacatc acatggctga gcaatgggca    60
cg    62

<210> SEQ ID NO 72
<211> LENGTH: 103
<212> TYPE: DNA
<213> ORGANISM: Artificial sequence
<220> FEATURE:
<223> OTHER INFORMATION: Synthetic nucleic acid sequence

<400> SEQUENCE: 72
ccggcccggc cgcggggagc cccgcttcat cgcagtgggc tacgtggacg acacgcagtt    60
cgtgcggttc gacagcgacg ccgcgagcca gaggatggag ccg    103

<210> SEQ ID NO 73
<211> LENGTH: 108
<212> TYPE: DNA
<213> ORGANISM: Artificial sequence
<220> FEATURE:
<223> OTHER INFORMATION: Synthetic nucleic acid sequence

<400> SEQUENCE: 73
ccggcccggc cgcggggagc cccgcttcat cgcagtgggc tacgtggact ggacgacacg    60
cagttcgtgc ggttcgacag cgacgccgcg agccagagga tggagccg    108

<210> SEQ ID NO 74
<211> LENGTH: 102
<212> TYPE: DNA
<213> ORGANISM: Artificial sequence
<220> FEATURE:
<223> OTHER INFORMATION: Synthetic nucleic acid sequence

<400> SEQUENCE: 74
aggagccgcg ggcgccatgg atagagcagg aggggccgga gtattgggac cgggagacac    60
agatctccaa gaccaacaca cagacttacc gagagagcct gc    102

```
<210> SEQ ID NO 75
<211> LENGTH: 110
<212> TYPE: DNA
<213> ORGANISM: Artificial sequence
<220> FEATURE:
<223> OTHER INFORMATION: Synthetic nucleic acid sequence

<400> SEQUENCE: 75
aggagccgcg ggcgccatgg atagagcagg aggggccgga gtattgggac cgggagacac      60
agatctccaa gaccaacaca cagacttacc gagttaccga gagagcctgc                 110

<210> SEQ ID NO 76
<211> LENGTH: 108
<212> TYPE: DNA
<213> ORGANISM: Artificial sequence
<220> FEATURE:
<223> OTHER INFORMATION: Synthetic nucleic acid sequence

<400> SEQUENCE: 76
gtgcgtggag tggctccgca gacacctgga gaacgggaag gagacgctgc agcgcgcggg      60
taccaggggc agtggggagc cttccccatc tcctataggt cgccggggg                  108

<210> SEQ ID NO 77
<211> LENGTH: 107
<212> TYPE: DNA
<213> ORGANISM: Artificial sequence
<220> FEATURE:
<223> OTHER INFORMATION: Synthetic nucleic acid sequence

<400> SEQUENCE: 77
gtgcgtggag tggctccgca gacacctgga gaacgggaag gagacgctgc agcgcgcggg      60
taccggggca gtggggagcc ttccccatct cctataggtc gccgggg                    107

<210> SEQ ID NO 78
<211> LENGTH: 174
<212> TYPE: DNA
<213> ORGANISM: Artificial sequence
<220> FEATURE:
<223> OTHER INFORMATION: Synthetic nucleic acid sequence

<400> SEQUENCE: 78
ggacctcctg gagcagaggc gggccgcggt ggacacctac tgcagacaca actacggggt      60
tggtgagagc ttcacagtgc agcggcgagg tgagcgcggc gcgggcggg gcctgagtcc      120 ctgtaagcgg agaatctgag tgtgtgtgtg tgtgtgtgtg tgtgtgtgtg taag            174

<210> SEQ ID NO 79
<211> LENGTH: 179
<212> TYPE: DNA
<213> ORGANISM: Artificial sequence
<220> FEATURE:
<223> OTHER INFORMATION: Synthetic nucleic acid sequence

<400> SEQUENCE: 79
ggacttcctg gaagacaggc gggccgcggt ggacacctac tgcagacaca actacggggt      60
tggtgagagc ttcacagtgc agcggcgagg tgagcgcggc gcgggcggg gcctgagtcc      120 ctgtgagctg ggaatctgag tgtgtgtgtg tgtgtgtgtg tgtgtgtgtg tgtgtgtgt      179

<210> SEQ ID NO 80
<211> LENGTH: 179
<212> TYPE: DNA
<213> ORGANISM: Artificial sequence
<220> FEATURE:
```

<223> OTHER INFORMATION: Synthetic nucleic acid sequence

<400> SEQUENCE: 80

```
ggacttcctg gaagacaggc gggccgcggt ggacacctac tgcagacaca actacggggt      60
tggtgagagc ttcacggtgc agcggcgagg tgagcgcggc gcggggcggg gcctgagtcc     120
ctgtgagctg ggaatctgag tgtgtgtgtg tgtgtgtgtg tgtgtgtgtg tgtgtgtgt      179
```

<210> SEQ ID NO 81
<211> LENGTH: 180
<212> TYPE: DNA
<213> ORGANISM: Artificial sequence
<220> FEATURE:
<223> OTHER INFORMATION: Synthetic nucleic acid sequence

<400> SEQUENCE: 81

```
cgacagccga cgccgcgagt ccgaggatgg cgccccgggc gccatggata gagcaggagg      60
ggccggagta ttgggaccgg aacacacaga tctgcaagac caacacacag acttaccgag     120
agagcctgcg gaacctgcgc ggctactaca accagagcga ggccgggtct cacatcatcc     180
```

<210> SEQ ID NO 82
<211> LENGTH: 180
<212> TYPE: DNA
<213> ORGANISM: Artificial sequence
<220> FEATURE:
<223> OTHER INFORMATION: Synthetic nucleic acid sequence

<400> SEQUENCE: 82

```
cgacagccga cgccgcgagt ccgaggatgg cgccccgggc gccatggata gagcaggagg      60
ggccggagta ttgggaccgg gagacacaga tctccaagac caacacacag acttaccgag     120
agagcctgcg gaacctgcgc ggctactaca accagagcga ggccgggtct cacaccctcc     180
```

<210> SEQ ID NO 83
<211> LENGTH: 448
<212> TYPE: DNA
<213> ORGANISM: Artificial sequence
<220> FEATURE:
<223> OTHER INFORMATION: Synthetic nucleic acid sequence

<400> SEQUENCE: 83

```
atgcgggtca cggcgccccg aaccgtcctc ctgctgctct cgggagccct ggccctgacc      60
gagacctggg ccggctccca ctccatgagg tatttctaca ccgccatgtc ccggcccggc     120
cgcggggagc ccgcttcat cgcagtgggc tacgtggacg acacccagtt cgtgaggttc     180
gacagcgacg ccgcgagtcc gaggatggcg ccccgggcgc catggataga gcaggagggg     240
ccggagtatt gggaccggga gacacagatc tccaagacca acacacagac ttaccgagag     300
agcctgcgga acctgcgcgg ctactacaac cagagcgagg ccgggtctca cccctccag     360
aggatgtacg gctgcgacgt ggggccggac gggcgcctcc tccgcgggca tgaccagtcc     420
gcctacgacg gcaaggatta catcgccc                                       448
```

<210> SEQ ID NO 84
<211> LENGTH: 448
<212> TYPE: DNA
<213> ORGANISM: Artificial sequence
<220> FEATURE:
<223> OTHER INFORMATION: Synthetic nucleic acid sequence

<400> SEQUENCE: 84

```
atgcgggtca tggcgccccg aaccgtcctc ctgctgctct cgggagccct ggccctgacc      60
```

```
gagacctggg ccggctccca ctccatgagg tatttctaca ccgccatgtc ccggcccggc      120
cgcggggagc cccgcttcat cgcagtgggc tacgtggacg acacccagtt cgtgaggttc      180
gacagcgacg ccgcgagtcc gaggatggcg ccccgggcgc catggataga gcaggagggg      240
ccggagtatt gggaccggga gacacagatc tccaagacca acacacagac ttaccgagag      300
agcctgcgga acctgcgcgg ctactacaac cagagcgagg ccgggtctca caccctccag      360
aggatgtaag gctgcgacgt ggggccggac gggcgcctcc tccgcgggca tgaccagtcc      420
gcctacgacg gcaaggatta catcgccc                                         448
```